United States Patent
Degterev et al.

(10) Patent No.: US 9,701,646 B2
(45) Date of Patent: Jul. 11, 2017

(54) SMALL MOLECULE INHIBITORS OF PI3-KINASE SIGNALING

(71) Applicants: Tufts University, Boston, MA (US); Council of Scientific and Industrial Research, New Delhi (IN)

(72) Inventors: Alexei Degterev, Brookline, MA (US); Chepuri V. Ramana, Pune (IN); Jinbo Lee, Andover, MA (US); Yadagiri Kommagalla, Warangal (IN)

(73) Assignees: TUFTS UNIVERSITY, Boston, MA (US); COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/777,630

(22) PCT Filed: Mar. 18, 2014

(86) PCT No.: PCT/US2014/031016
§ 371 (c)(1),
(2) Date: Sep. 16, 2015

(87) PCT Pub. No.: WO2014/153337
PCT Pub. Date: Sep. 25, 2014

(65) Prior Publication Data
US 2016/0297777 A1    Oct. 13, 2016

Related U.S. Application Data

(60) Provisional application No. 61/802,960, filed on Mar. 18, 2013.

(51) Int. Cl.
*C07D 249/06*    (2006.01)
(52) U.S. Cl.
CPC ................................ *C07D 249/06* (2013.01)
(58) Field of Classification Search
CPC .................................................... C07D 249/06
See application file for complete search history.

(56) References Cited

PUBLICATIONS

Golub, 1999, Science, vol. 286, p. 531-537.*
Targeted Cacner Therapies Fact Sheet, retrieved from http://www.cancer.gov/about-cancer/treatment/types/targeted-gherapies/targeted-therapies-fact-sheet, retrieved Dec. 8, 2015.*
Cancer Prevention Overview, retrieved from http://www.cancer.gov/cancertopics/pdq/prevention/overview/patient, modified May 25, 2012.*
Voskoglou-Nomikos et al, 2003, Clinical Cancer Research, vol. 9, p. 4227-4239.*
Pubchem, Compound Summary for CID 11392406, CHEMBL465950, from https://pubchem.ncbi.nlm.nih.gov/summary/summary.cgi?cid=11392406, entire document, Oct. 26, 2006.
Calderone, V. et al., "Benzoyl and/or benzyl substituted 1,2,3-triazoles as potassium channel activators", *VIII, European Journal of Medicinal Chemistry*, 40(6):521-528 (Elsevier SAS, Italy, 2005).
International Search Report and Written Opinion from parent PCT application PCT/US2014/031016 dated Nov. 10, 2014.

* cited by examiner

*Primary Examiner* — Rebecca Anderson
*Assistant Examiner* — Karen Cheng
(74) *Attorney, Agent, or Firm* — Alan W. Steele

(57) ABSTRACT

Provided are certain 1,2,3-triazole and 1,2,3-triazole dimer analogs of DM-PIT-1 which are second-generation selective non-phosphoinositide small molecule inhibitors of phosphatidylinositol-3,4,5-trisphosphate (PIP3), including 1,2,3-triazoles represented by formula (I)

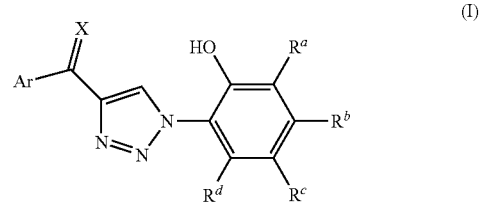

where:
Ar represents aryl or heteroaryl;
X represents O or S;
each of $R^a$, $R^b$, $R^c$, and $R^d$ independently represents hydrogen, halogen, $C_1$-$C_{10}$alkyl, —OH, —$CF_3$, aryl, amino, or nitro; and
Ar is optionally substituted with one or more substituents independently selected from the group consisting of halogen, $C_1$-$C_{10}$alkyl, —OH, —$CF_3$, amino, and nitro. Also provided are pharmaceutical compositions comprising compounds of the invention and a pharmaceutical carrier. Also provided are methods of inhibiting PIP3-mediated signaling in a cell and treating cancer using compounds of the invention.

14 Claims, 10 Drawing Sheets

DM-PIT-1
(PRIOR ART)

YK-NCL-176

YK-NCL-179

YK-NCL-240

YK-NCL-198

SMALL MOLECULE INHIBITORS OF PI3-KINASE SIGNALING

RELATED APPLICATIONS

This application is the U.S. national phase of International Patent Application No. PCT/US2014/031016, filed Mar. 18, 2014, which claims benefit of U.S. Provisional Patent Application No. 61/802,960, filed Mar. 18, 2013.

STATEMENT OF GOVERNMENT SUPPORT

This invention was made with government support under grant CA151881 awarded by the National Institutes of Health. The government has certain rights in the invention.

BACKGROUND OF THE INVENTION

Phosphoinositide 3-kinase (PI3K, also known as phosphatidylinositol-3-kinase and PI3-kinase) plays a critical role in many cellular functions, including survival, proliferation, metabolism, and motility. Cantley L C, *Science* 296:1655-7 (2002). Dysregulation of the PI3K pathway has been implicated in many human diseases. Hyper-activation of this pathway is known to play an important role in tumorigenesis, whereas deficiencies contribute to the development of type II diabetes. Therefore, this pathway offers promising targets for the development of drugs to combat these diseases.

Class I PI3Ks (α, β, and γ) are recruited to the plasma membrane in response to growth factor and hormone stimulation to mediate the phosphorylation of lipid phosphatidylinositol-4,5-bisphosphate (PIP2), generating phosphatidylinositol-3,4,5-trisphosphate (PIP3), which orchestrates multiple downstream intracellular signaling events. PIP3 signaling is terminated by the phosphatase PTEN, which dephosphorylates PIP3. Genetic alterations targeting PTEN are among the most frequent mutations in human cancers, indicating a critical role of uncontrolled signaling through PIP3 in tumorigenesis and metastasis. Maehama T et al., *Trends Cell Biol* 9:125-128 (1999). This conclusion is reinforced by transgenic studies establishing that loss of PTEN leads to tumorigenesis. Vivanco I et al., *Nat Rev Cancer* 2:489-501 (2002).

PIP3 controls a complex cellular signaling network regulating cell growth, proliferation, and survival. PIP3 target proteins are located in the cytosol of unstimulated cells and are recruited to the membrane through pleckstrin-homology (PH) domain-mediated binding to newly formed PIP3. Membrane translocation and activation of the PIP3 target proteins initiate a variety of local responses, including assembly of signaling complexes and priming of protein kinase cascades. PIP3 regulates an array of PH domain-containing proteins, such as serine-threonine kinases Akt and PDK1, GRP1, GDP/GTP exchange factors of Rac and ADP ribosylating factor 6 (ARF6), and protein tyrosine kinases of the Bruton's tyrosine kinase (Btk) and Tec families. Park W S et al., *Mol Cell* 30:381-392 (2008); Varnai P et al., *J Cell Sci* 118:4879-4888 (2005); Lietzke S E et al., *Mol Cell* 6:385-394 (2000). This diversity in PIP3 signaling makes it one of the most important second messengers downstream from growth factor and oncogene signals.

Among the PIP3-controlled signaling proteins, the serine-threonine Akt/PKB (Akt) protein kinase family is of particular interest, because it has been found to play a central role in wide range of fundamental cellular functions including cell survival, growth, and energy metabolism. Datta S R et al., *Genes Dev* 13:2905-27 (1999); Scheid M P et al., *Nat Rev Mol Cell Biol* 2:760-8 (2001). The mechanism by which Akt protects cells from death is likely to be multifactorial, involving direct phosphorylation of multiple components of the cell-death machinery such as FOXO transcription factors, BAD, glycogen synthase kinase-3 (GSK-3), and caspase-9. Akt also enhances protein synthesis and cell growth by activating mTOR, which, in concert with another PIP3-binding kinase, PDK1, stimulates p70 ribosomal protein S6 kinase (p70S6K) and inhibits translational repressor eukaryotic initiation factor 4E-binding protein 1 (4EBP1). Cardone M H et al. *Science* 282:1318-21 (1998); Cross D A et al. *Nature* 378:785-9 (1995); Datta S R et al. *Cell* 91:231-241 (1997); McManus E J et al. *Nat Cell Biol* 4:E214-216 (2002); Tee A R et al. *Proc Natl Acad Sci USA* 99:13571-6 (2002).

Activation of the Rac family or ARF6 by local gradients of PIP3 plays a major role in remodeling the actin cytoskeleton for directional motility in response to chemotactic agents and growth stimulation. These mechanisms play an important role in enhanced motility of cancer cells and cancer metastasis. Etienne-Manneville S et al. *Nature* 420: 629-35 (2002); Hornstein I et al. *Cell Signal* 16:1-11 (2004); Venkateswarlu K et al. *Biochem J* 345 Pt 3:719-24 (2004).

Although lipid-protein interactions mediate PI3K signaling and are frequently deregulated in cancer, most therapeutic strategies targeting the PI3K pathway have focused on inhibitors for downstream targets, including PDK1 and Akt. Peifer C et al., *Chem Med Chem* 3:1810-1838 (2008); Yang L. et al., *Cancer Res* 64:4394-4399. Phospholipid-protein interactions have not been as actively targeted, even though lipid molecules are among the most important classes of second messengers.

We recently discovered selective non-phosphoinositide small molecule PIP3 inhibitors, termed PITenins (PITs). US Pat. App. 2012/0016033 A1; US Pat. App. 2013/0036033; Miao B et al., *Oncogene* 31:4317-4332 (2012). PIT-1, selected in a screen of about 50,000 small molecules by using a PIP3/Akt PH domain binding assay, and its derivative DM-PIT-1 have been extensively characterized. PIT-1 and DM-PIT-1 effectively inhibit cancer cell survival and induces cell apoptosis by specifically inhibiting PIP3-dependent PI3K-PDK1-Akt signaling, resulting in significant anti-tumor activity in vivo.

SUMMARY OF THE INVENTION

An aspect of the invention is a compound represented by formula (II), or a pharmaceutically acceptable salt thereof

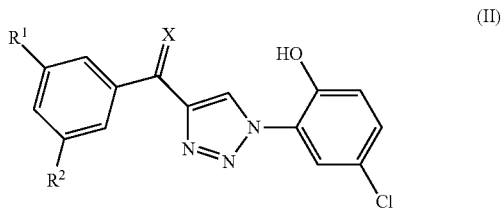

wherein:
R[1] and R[2] independently represent hydrogen, halogen, —OH, or —CF$_3$; and
X represents O or S.

An aspect of the invention is a compound represented by formula (III), or a pharmaceutically acceptable salt thereof

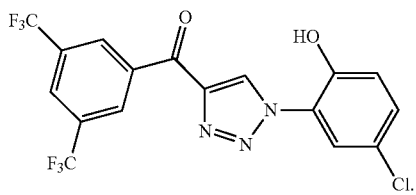

(III)

An aspect of the invention is a compound represented by formula (IV), formula (V), or formula (VI), or a pharmaceutically acceptable salt thereof

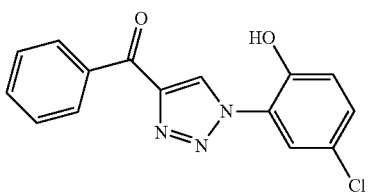

(IV)

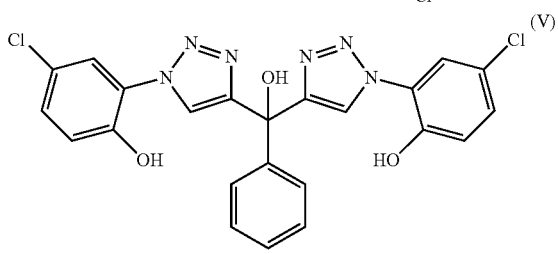

(V)

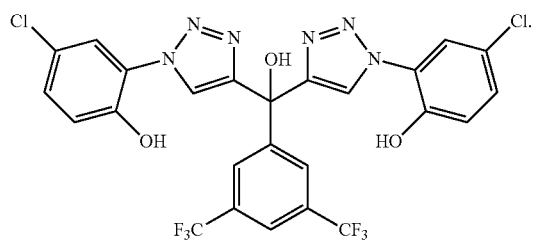

(VI)

An aspect of the invention is a compound, or a pharmaceutically acceptable salt thereof, selected from the group consisting of

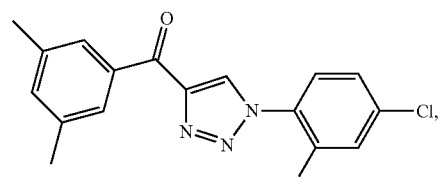

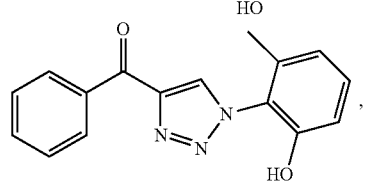

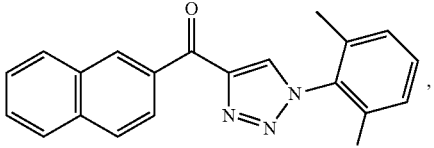

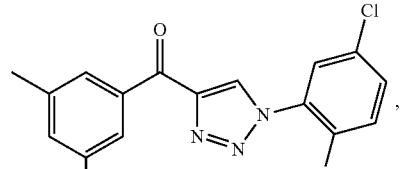

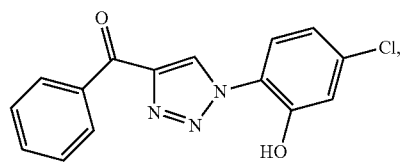

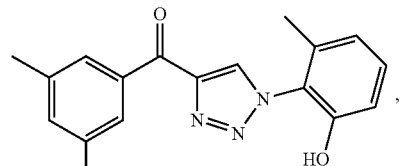

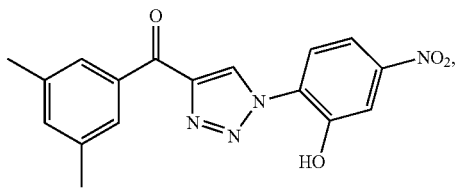

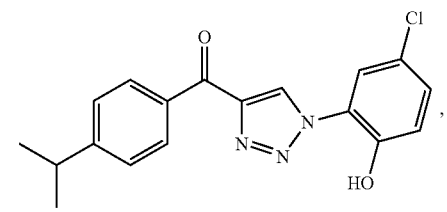

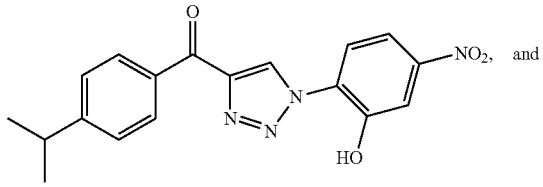

and

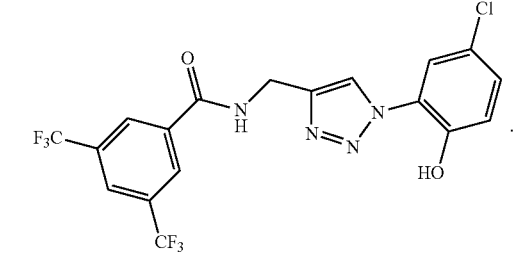

An aspect of the invention is a compound, or a pharmaceutically acceptable salt thereof, selected from the group consisting of

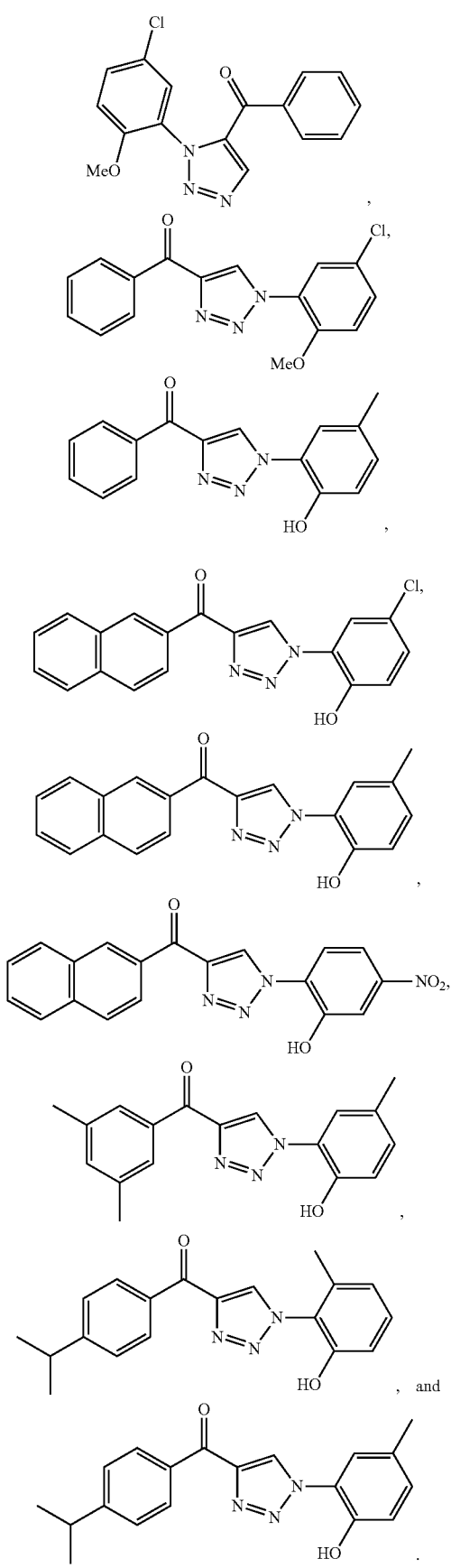
,
An aspect of the invention is a compound, or a pharmaceutically acceptable salt thereof, selected from the group consisting of
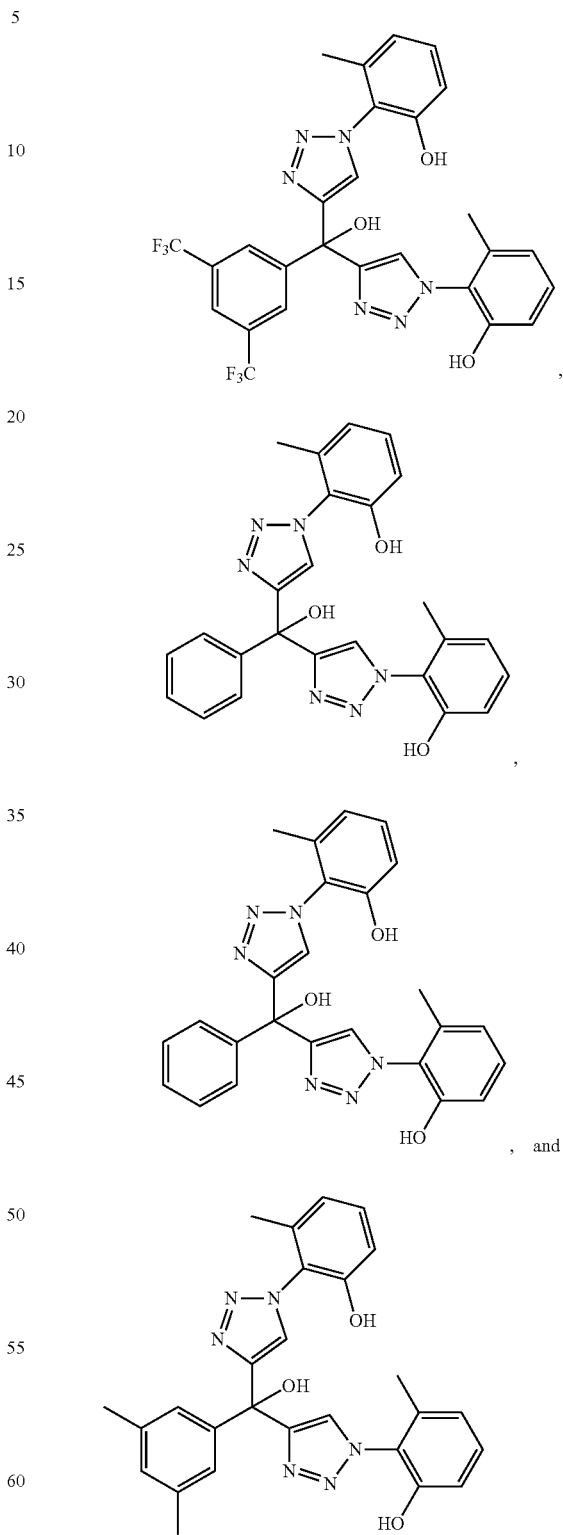
, and
An aspect of the invention is a compound, or a pharmaceutically acceptable salt thereof, selected from the group consisting of

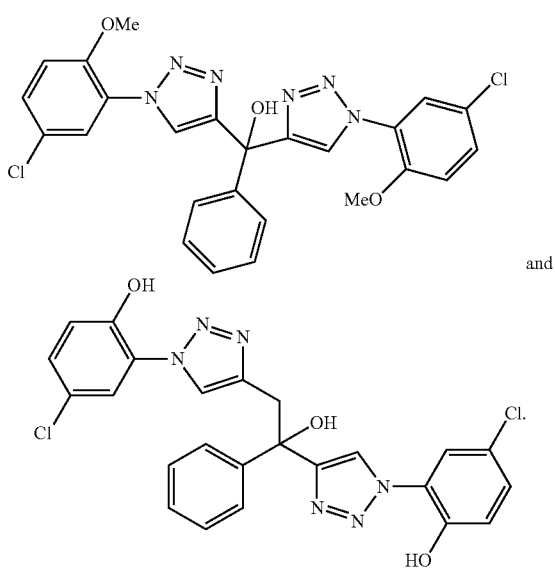

An aspect of the invention is a pharmaceutical composition, comprising a compound of the invention, or a pharmaceutically acceptable salt thereof, and a pharmaceutically acceptable carrier.

An aspect of the invention is a method of inhibiting PIPS-mediated signaling in a cell, comprising contacting a cell with an effective amount of a compound of the invention.

An aspect of the invention is a method of treating a cancer, comprising administering to a subject in need thereof a therapeutically effective amount of a compound of the invention, or a pharmaceutically acceptable salt thereof.

DETAILED DESCRIPTION OF THE INVENTION

Figure 1:
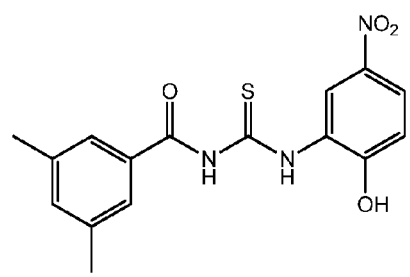
FIG. 1 depicts structures of compounds DM-PIT-1 (prior art), NCL-176, NCL-179, NCL-198, and NCL-240.
Figure 1:
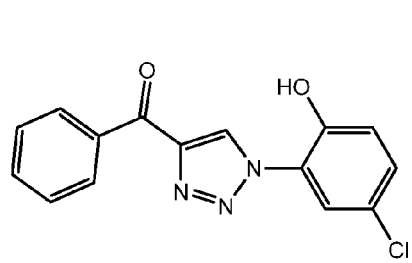
Figure 1:
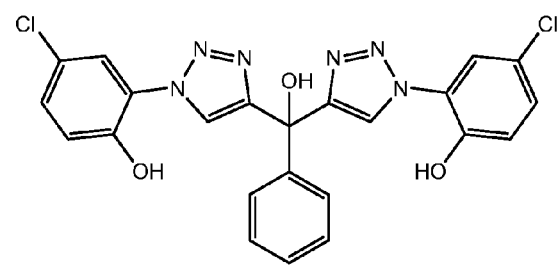
Figure 1:
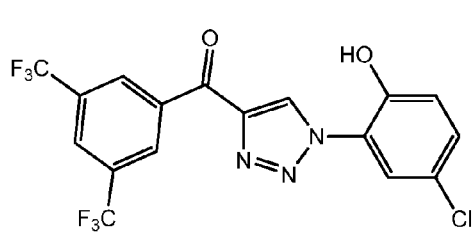
Figure 1:
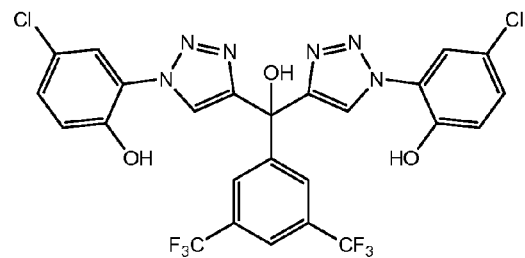

We have recently described a first generation novel inhibitor of the PI3K pathway N-[(2-hydroxy-5-nitrophenyl)amino]carbonothioyl-3,5-dimethylbenzamide (DM-PIT-1) capable of successfully inhibiting tumor growth with promising in vitro and in vivo results. US Pat. App. 2012/0016033 A1; US Pat. App. 2013/0036033; Miao B et al., *Oncogene* 31:4317-4332 (2012). DM-PIT-1 is a small molecule inhibitor preventing $PIP_3$/PH interaction. Despite the excellent apoptotic, anti-proliferative, and migration suppressive properties of the compound, studies leading to the present invention were undertaken to explore and seek to improve activity and pharmaceutical features of this new class of drug.

It was discovered, in accordance with the instant invention, that certain 1,2,3-triazole and 1,2,3-triazole dimer analogs of DM-PIT-1 are of particular interest. For example, 1,2,3-triazoles represented by the following general formula (I) were identified as potential second-generation PITenins (PITs)

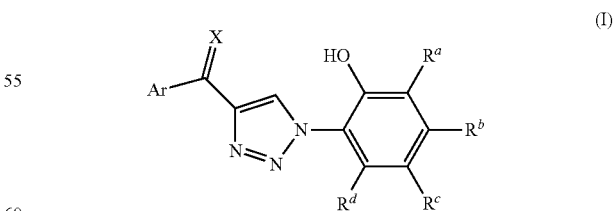

where:
Ar represents aryl or heteroaryl;
X represents O or S;
each of $R^a$, $R^b$, $R^c$, and $R^d$ independently represents hydrogen, halogen, $C_1$-$C_{10}$alkyl, —OH, —$CF_3$, aryl, amino, or nitro; and Ar is optionally substituted with one or more substituents independently selected from the group consisting of halogen, $C_1$-$C_{10}$alkyl, —OH, —CF$_3$, amino, and nitro.

In one embodiment, Ar is phenyl.

In one embodiment, Ar is heteroaryl.

In one embodiment, Ar is selected from the group consisting of pyridinyl, pyrimidinyl, and thiophenyl.

For example, the invention specifically contemplates the compounds:

(1-(2-hydroxyphenyl)-1H-1,2,3-triazol-4-yl)(phenyl)methanone;

(1-(2-hydroxyphenyl)-1H-1,2,3-triazol-4-yl)(pyridin-2-yl)methanone;

(1-(2-hydroxyphenyl)-1H-1,2,3-triazol-4-yl)(pyridin-3-yl)methanone;

(1-(2-hydroxyphenyl)-1H-1,2,3-triazol-4-yl)(pyridin-3-yl)methanone;

(1-(2-hydroxyphenyl)-1H-1,2,3-triazol-4-yl)(pyrimidin-4-yl)methanone;

(1-(2-hydroxyphenyl)-1H-1,2,3-triazol-4-yl)(pyrimidin-5-yl)methanone;

(1-(2-hydroxyphenyl)-1H-1,2,3-triazol-4-yl)(thiophen-2-yl)methanone; and (1-(2-hydroxyphenyl)-1H-1,2,3-triazol-4-yl)(thiophen-3-yl)methanone, substituted derivatives thereof, and pharmaceutically acceptable salts thereof.

An aspect of the invention is a compound represented by formula (II), or a pharmaceutically acceptable salt thereof

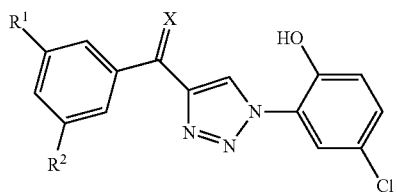

(II)

wherein:

$R^1$ and $R^2$ independently represent hydrogen, halogen, —OH, or —CF$_3$; and

X represents O or S.

In one embodiment, X is O.

In one embodiment, X is S.

In one embodiment, $R^1$ is —CF$_3$.

In one embodiment, each of $R^1$ and $R^2$ is —CF$_3$.

The compound of formula II wherein X is O and each of $R^1$ and $R^2$ is hydrogen corresponds to compound YK-NCL-176 (also referred to as NCL-176), described further herein below.

The compound of formula II wherein X is O and each of $R^1$ and $R^2$ is —CF$_3$ corresponds to compound YK-NCL-240 (also referred to as NCL-240), described further herein below.

An aspect of the invention is the compound represented by formula (III), or a pharmaceutically acceptable salt thereof

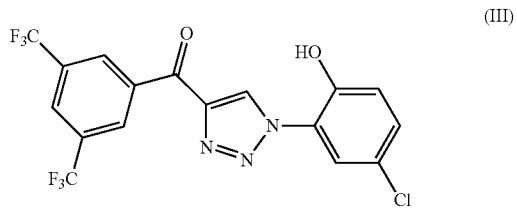 [SMILES: O=C(c1cc(C(F)(F)F)cc(C(F)(F)F)c1)c1cn(-c2cc(Cl)ccc2O)nn1]

(III)

i.e., the compound YK-NKL-240.

An aspect of the invention is a compound represented by formula (IV), formula (V), or formula (VI), or a pharmaceutically acceptable salt thereof

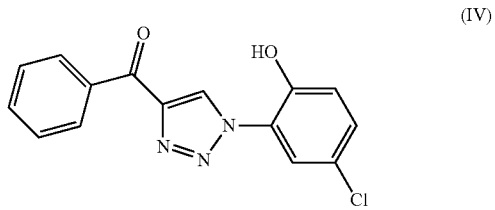

(IV)

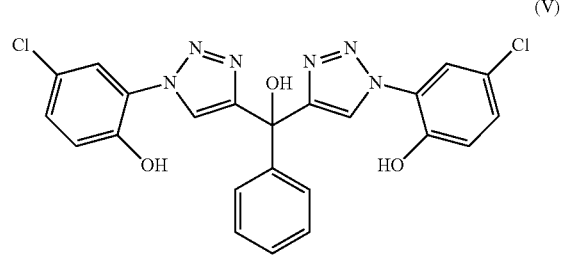

(V)

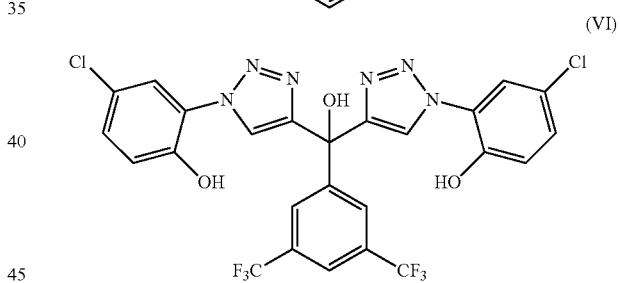

(VI)

where the compound represented by formula (IV) corresponds to compound YK-NCL-176, the compound represented by formula (V) corresponds to compound YK-NCL-179 (also referred to as NCL-179) described further herein below, and the compound represented by formula (VI) corresponds to compound YK-NCL-198 (also referred to as NCL-198) described further herein below.

An aspect of the invention is a compound, or a pharmaceutically acceptable salt thereof, selected from the group consisting of

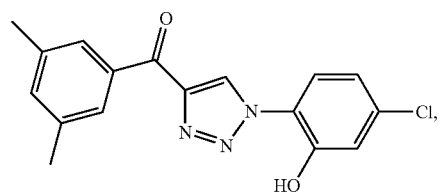

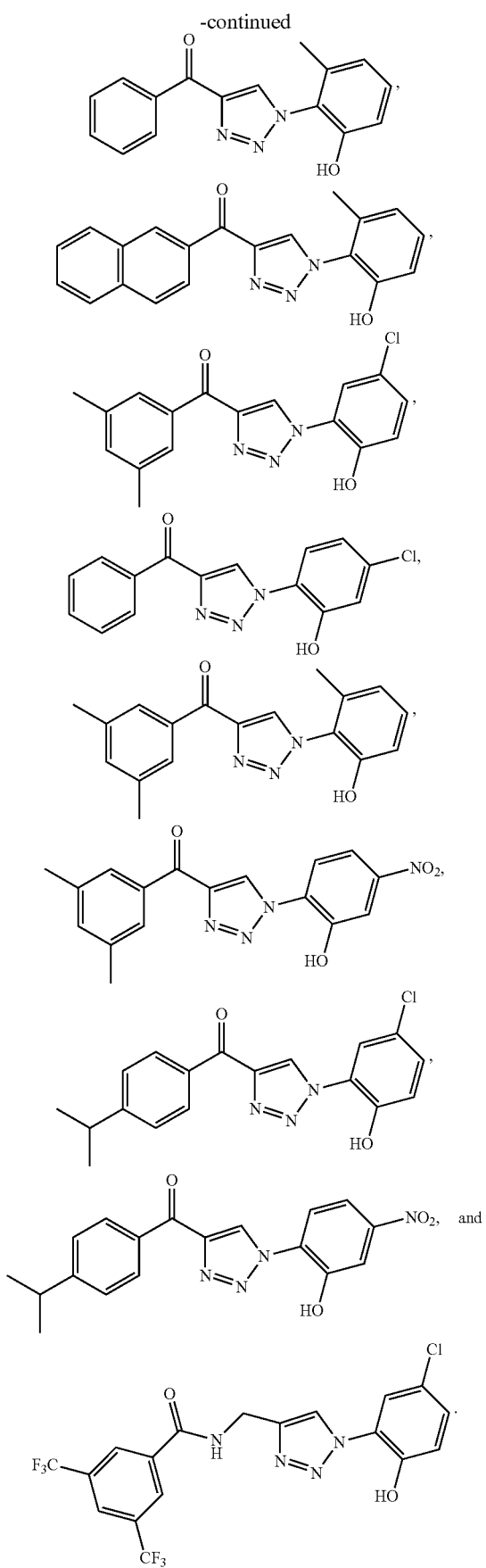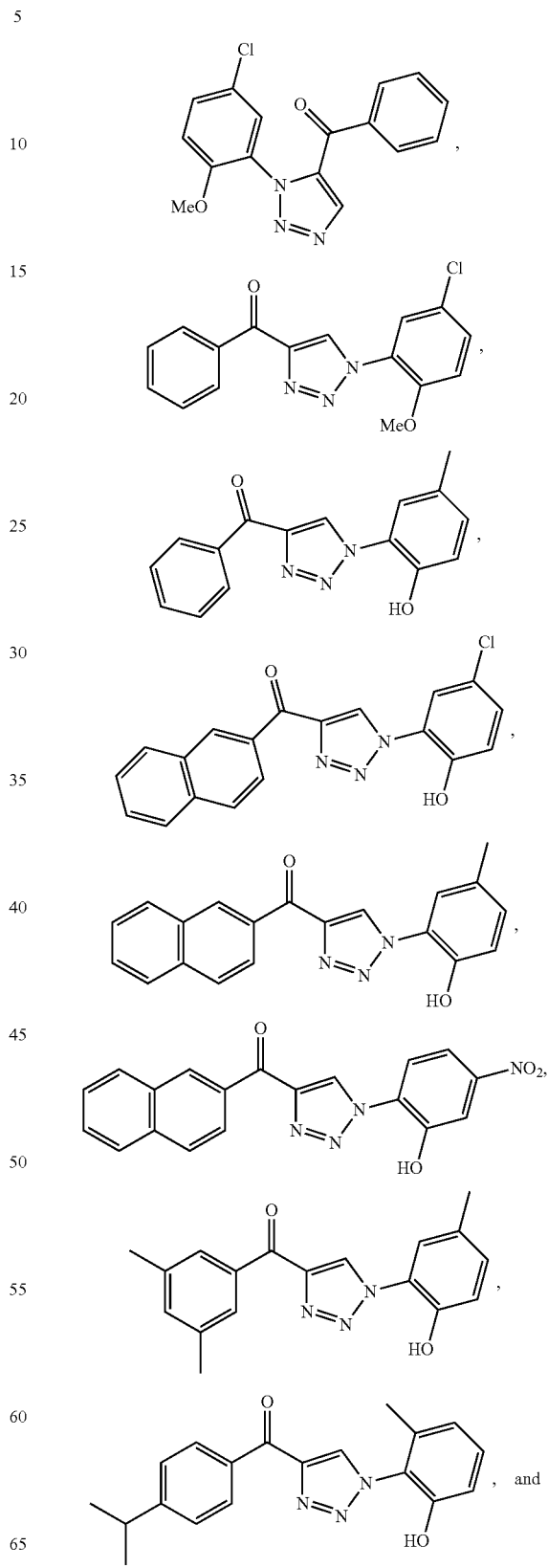
An aspect of the invention is a compound, or a pharmaceutically acceptable salt thereof, selected from the group consisting of

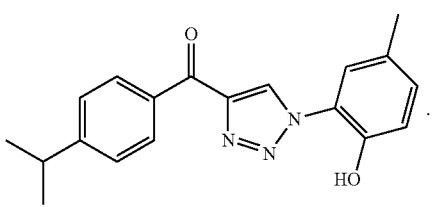

An aspect of the invention is a compound, or a pharmaceutically acceptable salt thereof, selected from the group consisting of

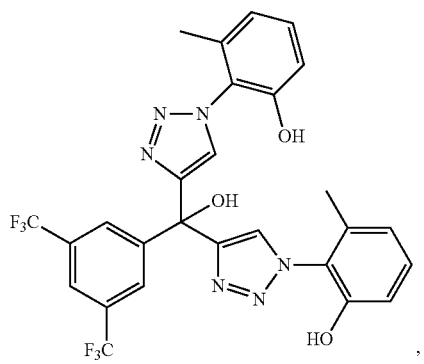

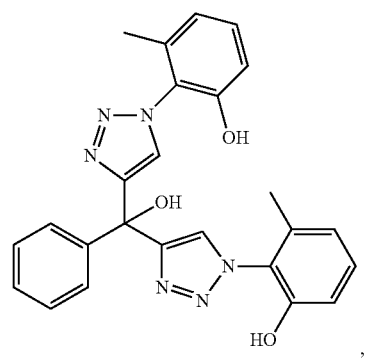

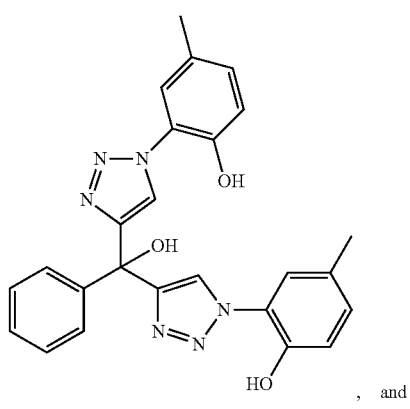

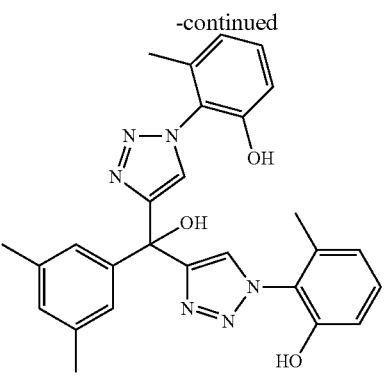

An aspect of the invention is a compound, or a pharmaceutically acceptable salt thereof, selected from the group consisting of

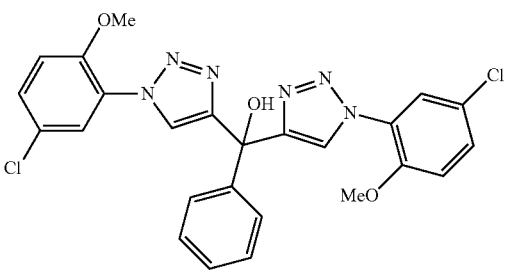

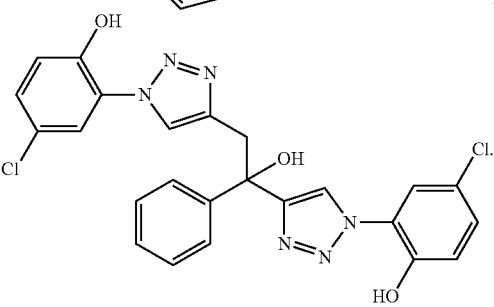

and

Collectively, all of the foregoing compounds, including compounds of formulas I, II, III, IV, V, and VI, as well as pharmaceutically acceptable salts thereof, are referred to herein as compounds of the invention.

An aspect of the invention is a pharmaceutical composition, comprising a compound of the invention, or a pharmaceutically acceptable salt thereof, and a pharmaceutically acceptable carrier.

In an embodiment, the pharmaceutical composition comprises a compound of formula (I), or a pharmaceutically acceptable salt thereof, and a pharmaceutically acceptable carrier.

In an embodiment, the pharmaceutical composition comprises a compound of formula (II), or a pharmaceutically acceptable salt thereof, and a pharmaceutically acceptable carrier.

In an embodiment, the pharmaceutical composition comprises a compound of formula (II), or a pharmaceutically acceptable salt thereof, and a pharmaceutically acceptable carrier.

In one embodiment, X is O.
In one embodiment, X is S.
In one embodiment, $R^1$ is —$CF_3$.
In one embodiment, each of $R^1$ and $R^2$ is —$CF_3$.

In an embodiment, the pharmaceutical composition comprises the compound of formula (III) (i.e., YK-NCL-240), or a pharmaceutically acceptable salt thereof, and a pharmaceutically acceptable carrier.

In an embodiment, the pharmaceutical composition comprises the compound of formula (IV) (i.e., YK-NCL-176), or a pharmaceutically acceptable salt thereof, and a pharmaceutically acceptable carrier.

In an embodiment, the pharmaceutical composition comprises the compound of formula (V) (i.e., YK-NCL-179), or a pharmaceutically acceptable salt thereof, and a pharmaceutically acceptable carrier.

In an embodiment, the pharmaceutical composition comprises the compound of formula (VI) (i.e., YK-NCL-198), or a pharmaceutically acceptable salt thereof, and a pharmaceutically acceptable carrier.

In an embodiment, the pharmaceutical composition comprises a compound, or a pharmaceutically acceptable salt thereof, selected from the group consisting of

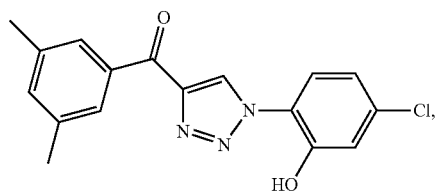

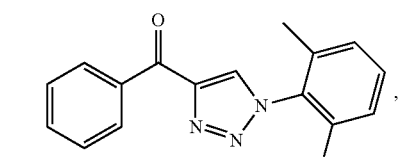

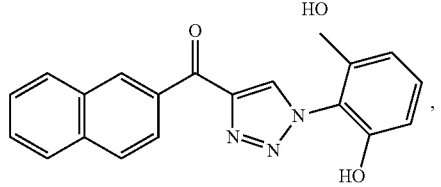

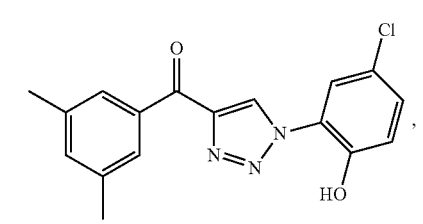

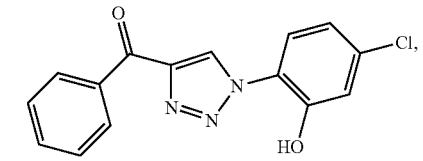

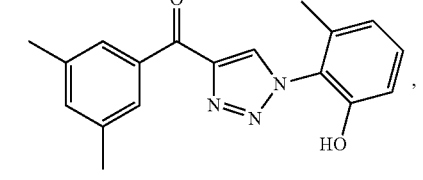

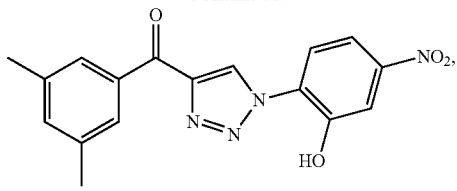

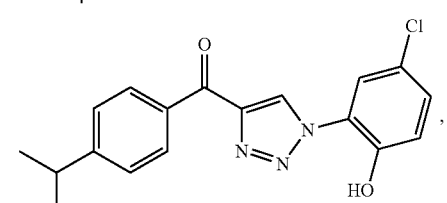

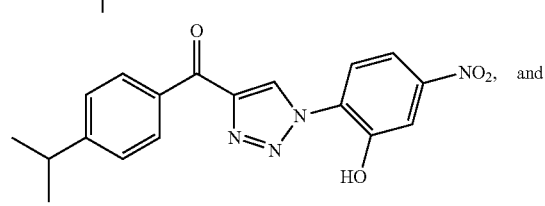 and

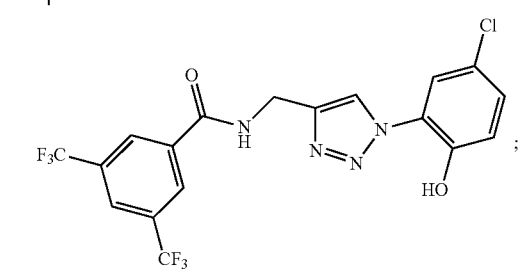

and a pharmaceutically acceptable carrier.

In an embodiment, the pharmaceutical composition comprises a compound, or a pharmaceutically acceptable salt thereof, selected from the group consisting of

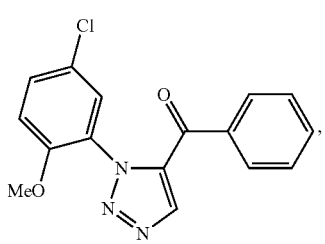

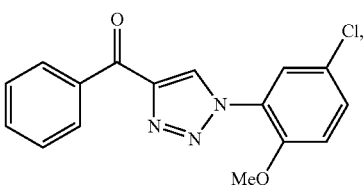

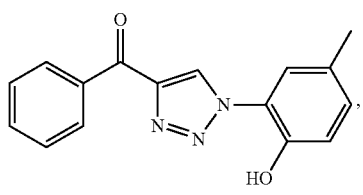 [SMILES: COc1ccc(Cl)cc1-n1cc(C(=O)c2ccccc2)nn1]

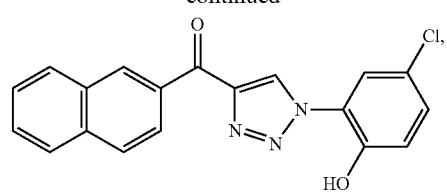

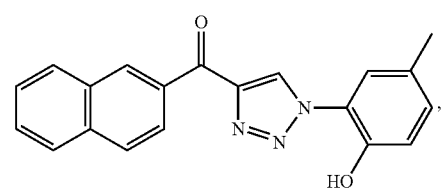 [SMILES: O=C(c1ccc2ccccc2c1)c1cn(-c2cc(Cl)ccc2O)nn1]

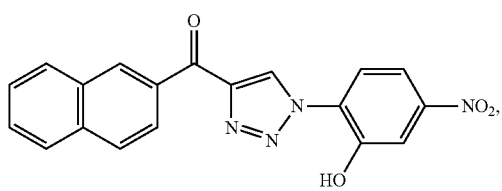 [SMILES: O=C(c1ccc2ccccc2c1)c1cn(-c2ccc([N+](=O)[O-])cc2O)nn1]

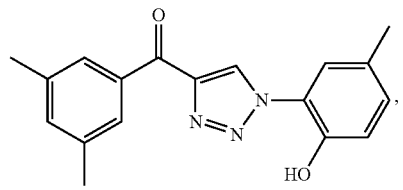 [SMILES: Cc1cc(C)cc(C(=O)c2cn(-c3cc(Cl)ccc3O)nn2)c1]

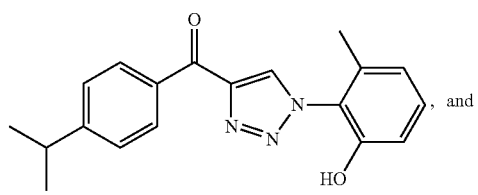

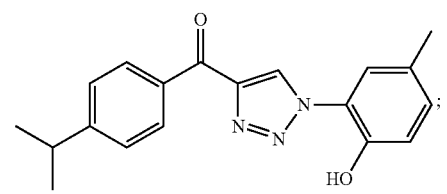

and a pharmaceutically acceptable carrier.

In an embodiment, the pharmaceutical composition comprises a compound, or a pharmaceutically acceptable salt thereof, selected from the group consisting of

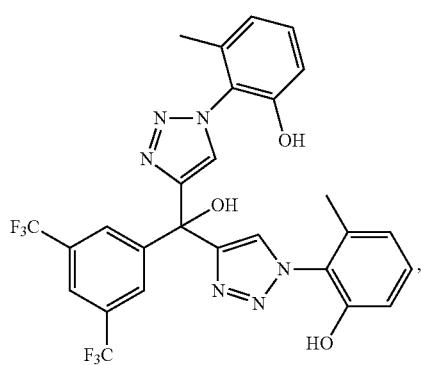

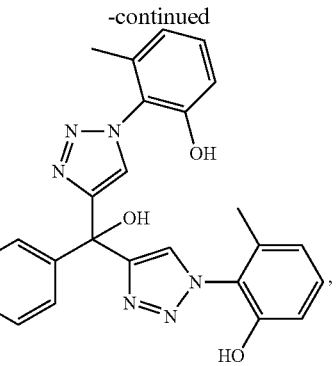

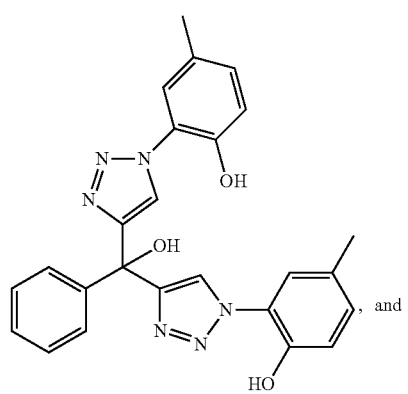

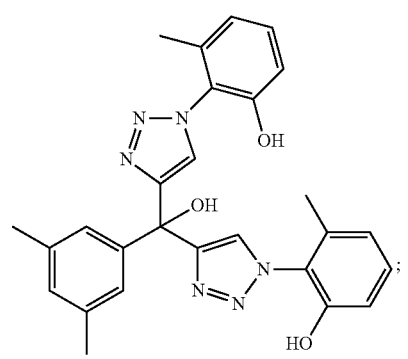

and a pharmaceutically acceptable carrier.

In an embodiment, the pharmaceutical composition comprises a compound, or a pharmaceutically acceptable salt thereof, selected from the group consisting of

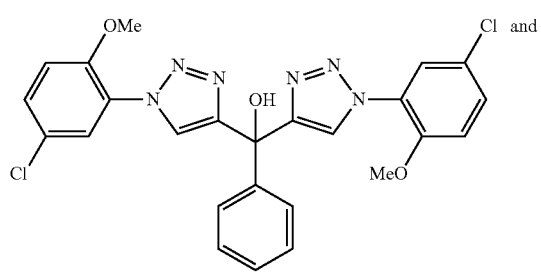

-continued

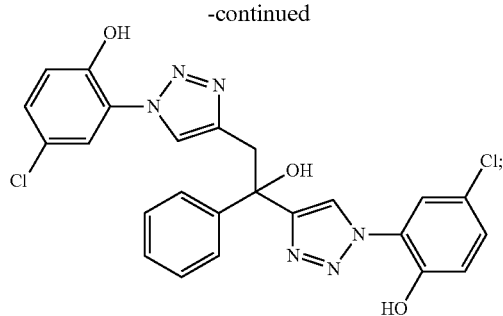

and a pharmaceutically acceptable carrier.

An aspect of the invention is a method of inhibiting PIPS-mediated signaling in a cell, comprising contacting a cell with an effective amount of a compound of the invention, or a pharmaceutically acceptable salt thereof.

In an embodiment, the method comprises contacting a cell with an effective amount of a compound of formula (I), or a pharmaceutically acceptable salt thereof.

In an embodiment, the method comprises contacting a cell with an effective amount of a compound of formula (II), or a pharmaceutically acceptable salt thereof.

In one embodiment, X is O.

In one embodiment, X is S.

In one embodiment, $R^1$ is —$CF_3$.

In one embodiment, each of $R^1$ and $R^2$ is —$CF_3$.

In an embodiment, the method comprises contacting a cell with an effective amount of a compound of formula (III) (i.e., YK-NCL-240), or a pharmaceutically acceptable salt thereof.

In an embodiment, the method comprises contacting a cell with an effective amount of a compound of formula (IV) (i.e., YK-NCL-176), or a pharmaceutically acceptable salt thereof.

In an embodiment, the method comprises contacting a cell with an effective amount of a compound of formula (V) (i.e., YK-NCL-179), or a pharmaceutically acceptable salt thereof.

In an embodiment, the method comprises contacting a cell with an effective amount of a compound of formula (VI) (i.e., YK-NCL-198), or a pharmaceutically acceptable salt thereof.

In an embodiment, the method comprises contacting a cell with an effective amount of a compound, or a pharmaceutically acceptable salt thereof, selected from the group consisting of

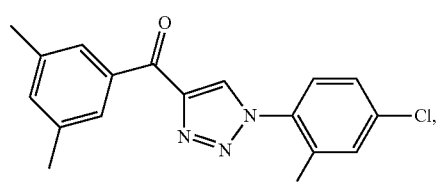

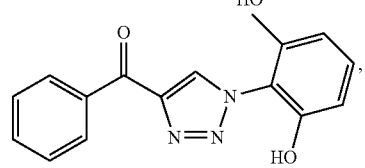

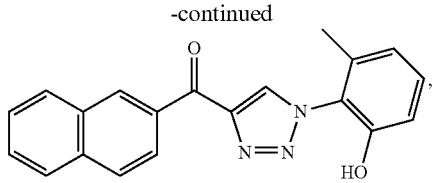

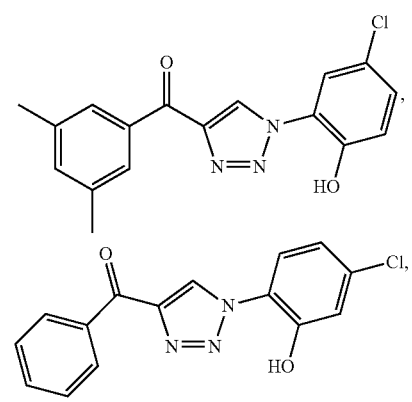

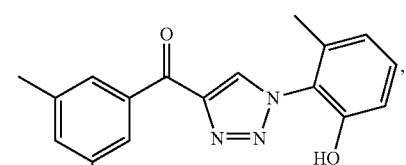

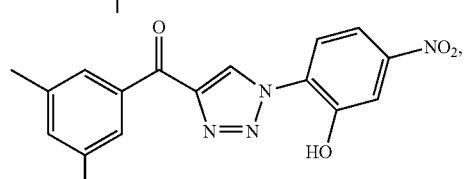

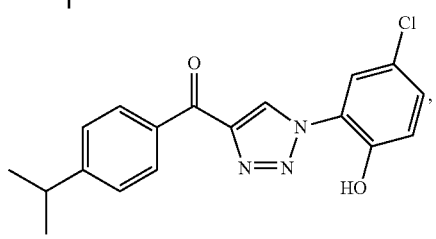

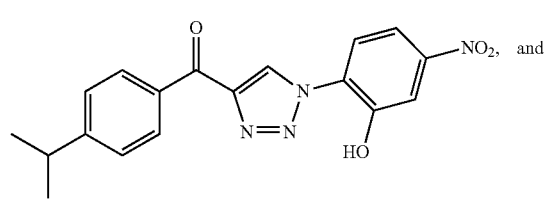

, and

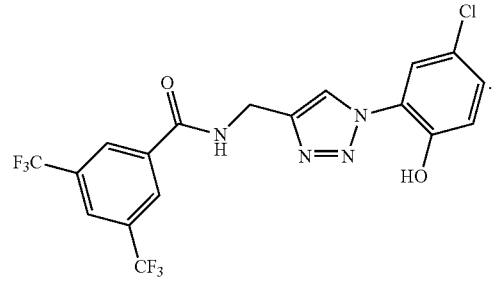

In an embodiment, the method comprises contacting a cell with an effective amount of a compound, or a pharmaceutically acceptable salt thereof, selected from the group consisting of

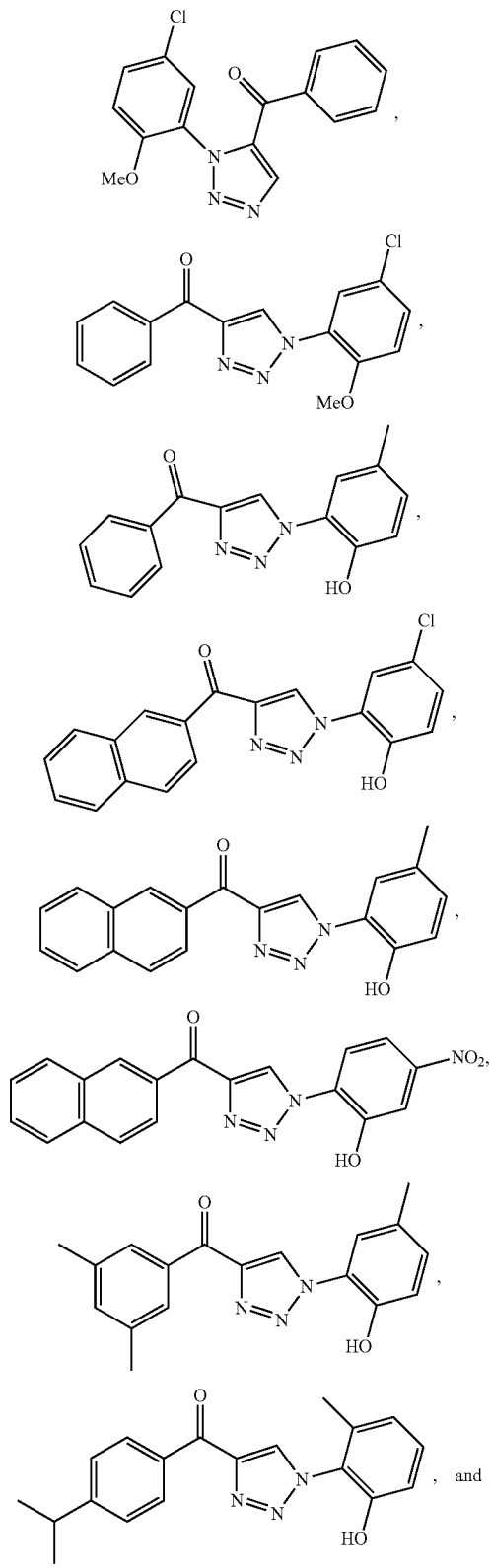

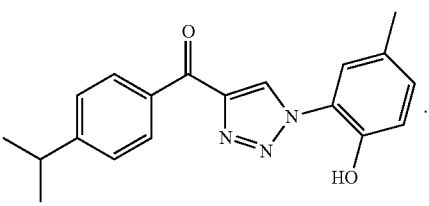

In an embodiment, the method comprises contacting a cell with an effective amount of a compound, or a pharmaceutically acceptable salt thereof, selected from the group consisting of

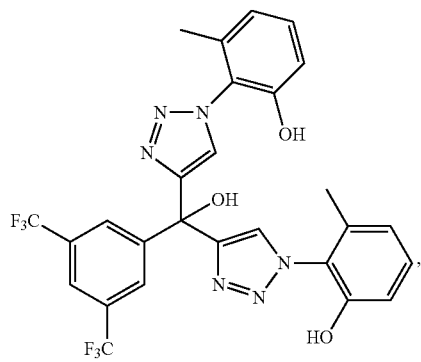

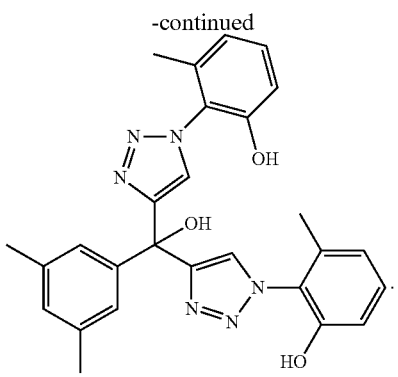

In an embodiment, the method comprises contacting a cell with an effective amount of a compound, or a pharmaceutically acceptable salt thereof, selected from the group consisting of

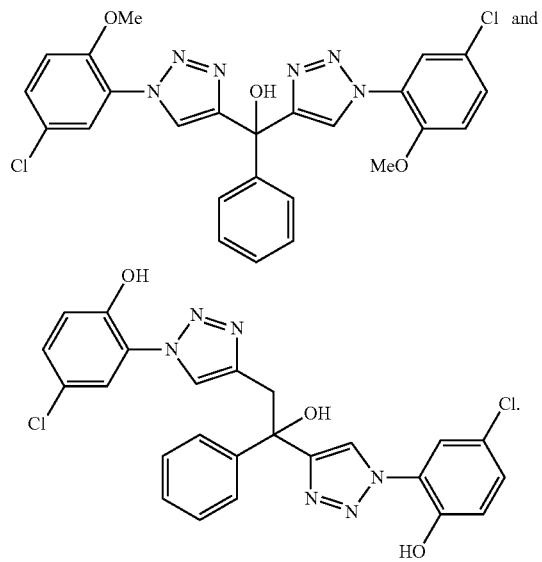

As used herein, "inhibit" or "inhibiting" means reduce by an objectively measurable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent compared to control.

As used herein, "PIP3-mediated signaling" refers to any PIP3-mediated intracellular event involving or following an interaction between PIP3 and a polypeptide that includes a pleckstrin homology domain. In this context, "following an interaction between PIP3 and a polypeptide that includes a pleckstrin homology domain" refers to any one or more events or steps downstream of PIP3 in the well known PI3K pathway. PIP3-mediated signaling thus includes such phenomena as the recruitment of any PIP3 target protein to the plasma membrane, binding of PIP3 to PH domains, polymerization of actin, assembly of signaling complexes, priming of protein kinase cascades. PIP3 target proteins are polypeptides and proteins that include at least one PH domain, and such molecules include, without limitation, Akt, GRP1, GDP/GTP exchange factors (GEFs) for Rac, Rho, and Cdc42 GTPases and ADP-ribosylating factor 6 (ARF6), and protein tyrosine kinases of the Bruton's tyrosine kinase (Btk) and Tec families. In one embodiment PIP3-mediated signaling specifically includes phosphorylation (activation) of Akt. In one embodiment PIP3-mediated signaling specifically refers to phosphorylation (activation) of Akt.

A pleckstrin homology (PH) domain is a ca. 100 to 120-amino acid modular fold found, for example, in over 250 human proteins. PH domains have few critically conserved amino acids but show remarkable conservation of three-dimensional structure. Crystal structures and nuclear magnetic resonance structures of several PH domains show a highly conserved three-dimensional organization, although sequence identities are only 7% to 23%. The core of each PH domain consists of a β-barrel of seven antiparallel β-strands and a COOH-terminal amphipathic α-helix. PH domains can bind to Gβγ subunits of heterotrimeric G proteins, to certain phosphotyrosine peptides, polyproline sequences, and phosphoinositides (PtdIns). A majority of PH domain members bind PtdIns weakly and nonspecifically, but a subclass of approximately 40 PH domain proteins shows high affinity for phosphoinositides. These PtdIns-binding PH domain proteins are important components of signal transduction pathways that regulate cancer cell growth and survival.

PtdIns-binding PH domains can be classified according to their binding specificity based on conserved positively charged residues in the phosphatidylinositol phosphate binding pocket and have $K_D$s in the range of 1 to 5 μmol/L. Group 1 PH domains specifically recognize PtdIns(3,4,5)P$_3$ (PIP3). Group 2 PH domains bind PtdIns(4,5)P$_2$ (PIP2) and also interact with other phosphoinositides, but because PIP2 is more abundant than 3-phosphorylated phosphoinositides, PH domains in group 2 are regulated by PIP2. Group 3 PH domains recognize PIP2 and PIP3. Group 4 PH domains have a low affinity for PtdIns binding. Group 2 PH domains mediate the effects of PIP2 on membrane trafficking and plasma membrane-cytoskeleton linkages, whereas group 1 and group 3 PH domains mediate the effects of PIP3 on cell signaling pathways that regulate growth and survival. Akt has a group 3 PH domain.

An aspect of the invention is a method of treating a cancer, comprising administering to a subject in need thereof a therapeutically effective amount of a compound of the invention, or a pharmaceutically acceptable salt thereof.

In an embodiment, the method comprises administering to a subject in need thereof a therapeutically effective amount of the compound of formula (I), or a pharmaceutically acceptable salt thereof.

In an embodiment, the method comprises administering to a subject in need thereof a therapeutically effective amount of the compound of formula (II), or a pharmaceutically acceptable salt thereof.

In one embodiment, X is O.
In one embodiment, X is S.
In one embodiment, $R^1$ is —CF$_3$.
In one embodiment, each of $R^1$ and $R^2$ is —CF$_3$.

In an embodiment, the method comprises administering to a subject in need thereof a therapeutically effective amount of the compound of formula (III) (i.e., YK-NCL-240), or a pharmaceutically acceptable salt thereof.

In an embodiment, the method comprises administering to a subject in need thereof a therapeutically effective amount of the compound of formula (IV) (i.e., YK-NCL-176), or a pharmaceutically acceptable salt thereof.

In an embodiment, the method comprises administering to a subject in need thereof a therapeutically effective amount of the compound of formula (V) (i.e., YK-NCL-179), or a pharmaceutically acceptable salt thereof.

In an embodiment, the method comprises administering to a subject in need thereof a therapeutically effective amount of the compound of formula (VI) (i.e., YK-NCL-198), or a pharmaceutically acceptable salt thereof.

In an embodiment, the method comprises administering to a subject in need thereof a therapeutically effective amount of a compound, or a pharmaceutically acceptable salt thereof, selected from the group consisting of

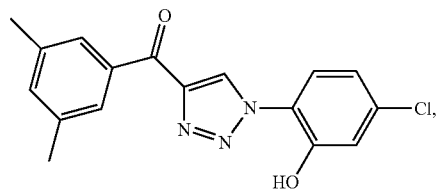

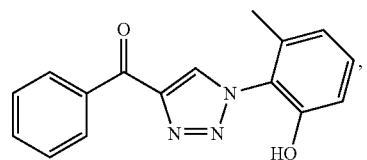

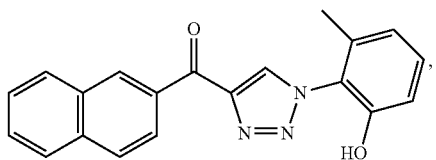

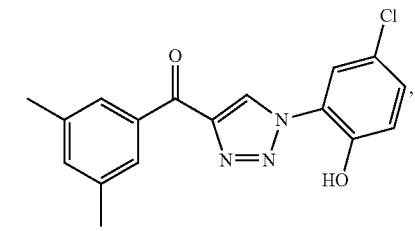

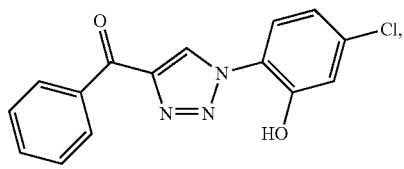

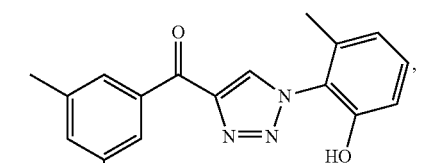

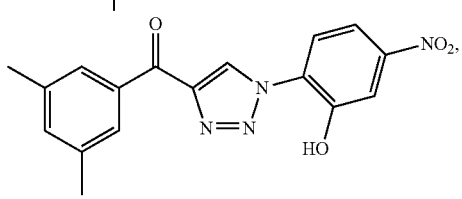

-continued

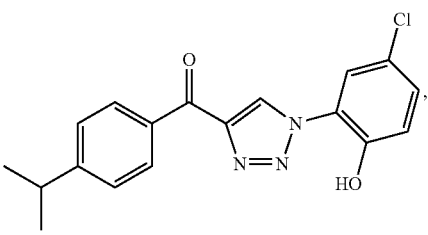

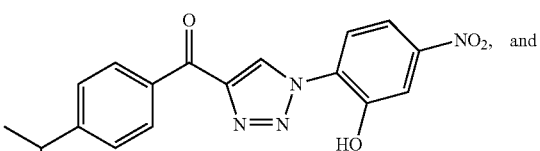

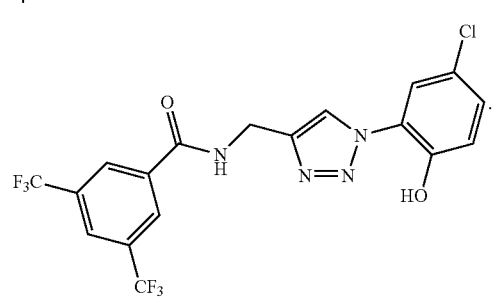

In an embodiment, the method comprises administering to a subject in need thereof a therapeutically effective amount of a compound, or a pharmaceutically acceptable salt thereof, selected from the group consisting of

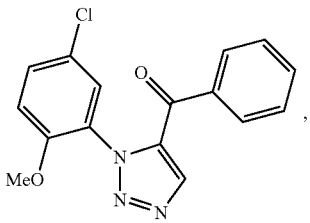

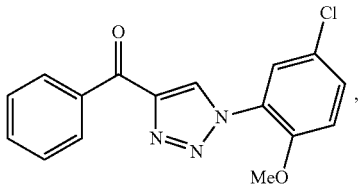

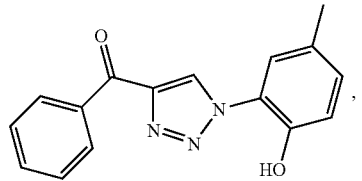

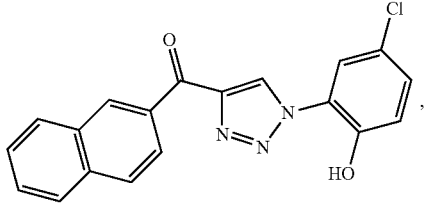

-continued

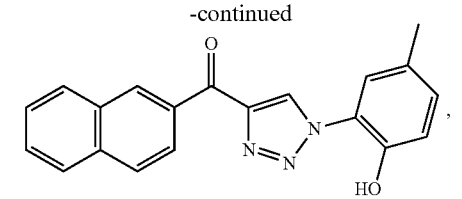,

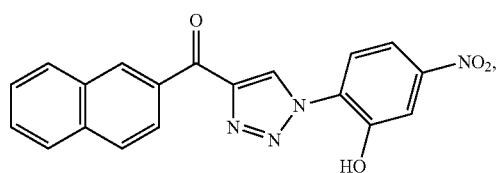,

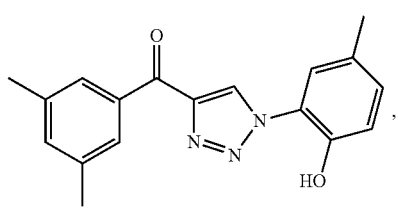,

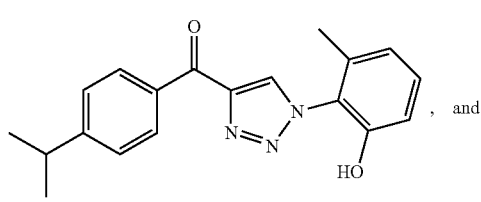.

In an embodiment, the method comprises administering to a subject in need thereof a therapeutically effective amount of a compound, or a pharmaceutically acceptable salt thereof, selected from the group consisting of

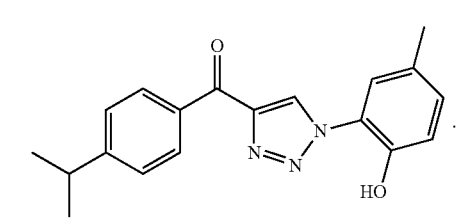,

-continued

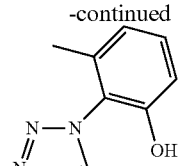,

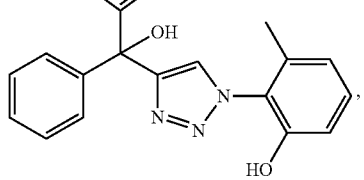,

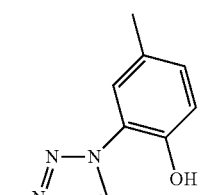, and

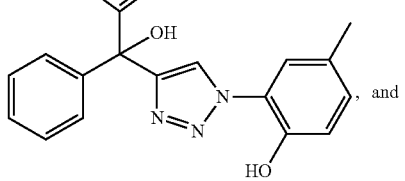.

In an embodiment, the method comprises administering to a subject in need thereof a therapeutically effective amount of a compound, or a pharmaceutically acceptable salt thereof, selected from the group consisting of

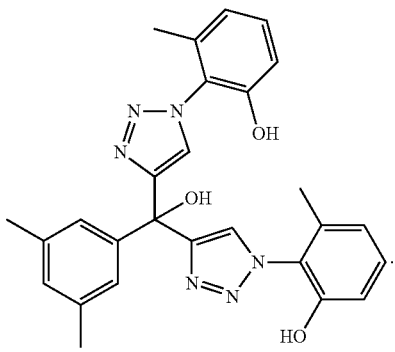.

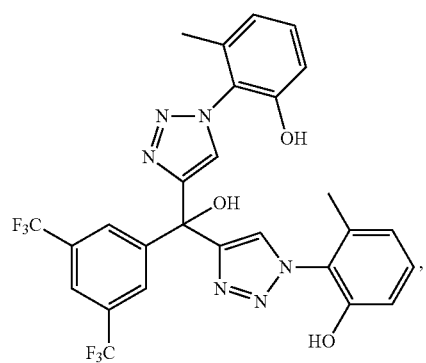

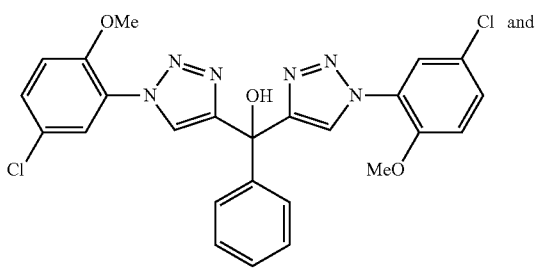 and

-continued

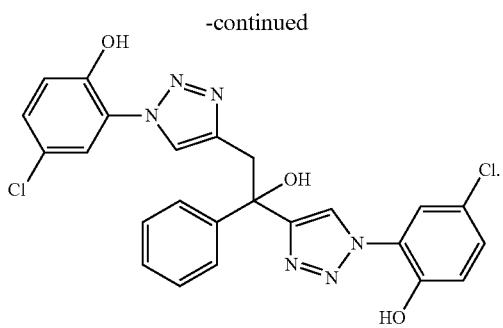

As used herein, the terms "treating" and "treat" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, "cancer" refers to an uncontrolled growth of cells which interferes with normal functioning of at least one bodily organ or system. Cancers which migrate from their original location and seed vital organs can eventually lead to the death of the subject through the functional deterioration of the affected organs. In certain embodiments a cancer is a tumor. Hemopoietic cancers, such as leukemia, are able to outcompete the normal hemopoietic compartments in a subject, thereby leading to hemopoietic failure (in the form of anemia, thrombocytopenia, neutropenia, and any combination thereof) ultimately causing death.

Cancers include, but are not limited to, basal cell carcinoma; biliary tract cancer; bladder cancer; bone cancer; brain cancer and other central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's lymphoma and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

A metastasis is a region of cancer cells, distinct in location from the primary tumor location, resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In one embodiment a subject is a human.

As used herein, a "subject having a cancer" refers to a subject that exhibits at least one objective manifestation of cancer. In one embodiment a subject having a cancer is a subject that has been diagnosed as having a cancer and is in need of treatment thereof. Methods of diagnosing cancer are well known and need not be described here in any detail.

As used herein, "administering" has its usual meaning and encompasses administering by any suitable route of administration, including, without limitation, intravenous, intramuscular, intraperitoneal, subcutaneous, direct injection (for example, into a tumor), mucosal, inhalation, oral, and topical.

As used herein, the phrase "effective amount" refers to any amount that is sufficient to achieve a desired biological effect. A therapeutically effective amount is an amount that is sufficient to achieve a desired therapeutic effect, e.g., to treat a cancer.

As used herein, a "non-phosphoinositide small molecule" refers to an organic molecule, other than a phosphoinositide or lipid-based molecule, having a molecular weight of less than or equal to 1500 Daltons. This term is understood specifically to exclude D-3-deoxy-phosphatidylinositol ether lipid (DPIEL, PX-316) (Meuillet E J et al., *Mol Cancer Ther* 2:389-99 (2003)), phosphatidylinositol ether lipid analogs (see, e.g., Castillo S S et al., *Cancer Res* 64:2782-92 (2004)), as well as NSC 348900 and analogs thereof disclosed in Mahadevan D et al. *Mol Cancer Ther* 7:2621-32 (2008).

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Other therapeutic agents which may be combined with compound of the invention include but are not limited to TRAIL and anti-cancer therapies.

Tumor necrosis factor (TNF)-related apoptosis-inducing ligand (TRAIL), also known as Apo2L, is a 281 amino acid-long member of the TNF family of cytokines that promotes apoptosis. Sheridan J P et al., *Science* 277:818-21 (1997). TRAIL induces apoptosis via death receptors in a wide variety of tumor cells but not in normal cells. Normal cells, but apparently not cancer cells, produce a "decoy receptor" that binds TRAIL but is incapable of transmitting its death message to the cell interior. It has been reported that TRAIL treatment results in significant growth suppression of TRAIL-sensitive human cancer xenografts in mice. Nagane M et al., *Apoptosis* 6:191-7 (2001). It has also been reported that TRAIL receptor (TRAIL-R) deficiency in mice promotes susceptibility to chronic inflammation and tumorigenesis. Finnberg N et al., *J Clin Invest* 118:11-23 (2008).

The compounds of the invention may also be administered in conjunction with an anti-cancer therapy. Anti-cancer therapies include cancer medicaments, radiation, and surgical procedures. As used herein, a "cancer medicament" refers to an agent which is administered to a subject for the purpose of treating a cancer. As used herein, "treating a cancer" includes preventing the development of a cancer, reducing the symptoms of cancer, and/or inhibiting the growth of an established cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

A chemotherapeutic agent can be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, IncelNX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

An immunotherapeutic agent may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA, but it is not so limited.

A cancer vaccine may be selected from the group consisting of EGF, anti-idiotypic cancer vaccines, gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys, but it is not so limited.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum close be used, that is, the highest safe close according to some medical judgment. Multiple closes per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such closes, even higher closes (or effective higher closes by a different, more localized delivery route) may be employed to the extent that patient tolerance permits. Multiple closes per day are contemplated to achieve appropriate systemic levels of compounds.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher closes may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor), mucosal, inhalation, and topical.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered close inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered close inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-close inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered close sprayer is attached. In one embodiment, the metered close is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured close of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically-acceptable carrier. The term "pharmaceutically-acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1. (1-(5-Chloro-2-hydroxyphenyl)-1H-1,2,3-triazol-4-yl)(phenyl)methanone (YK-NCL-176)

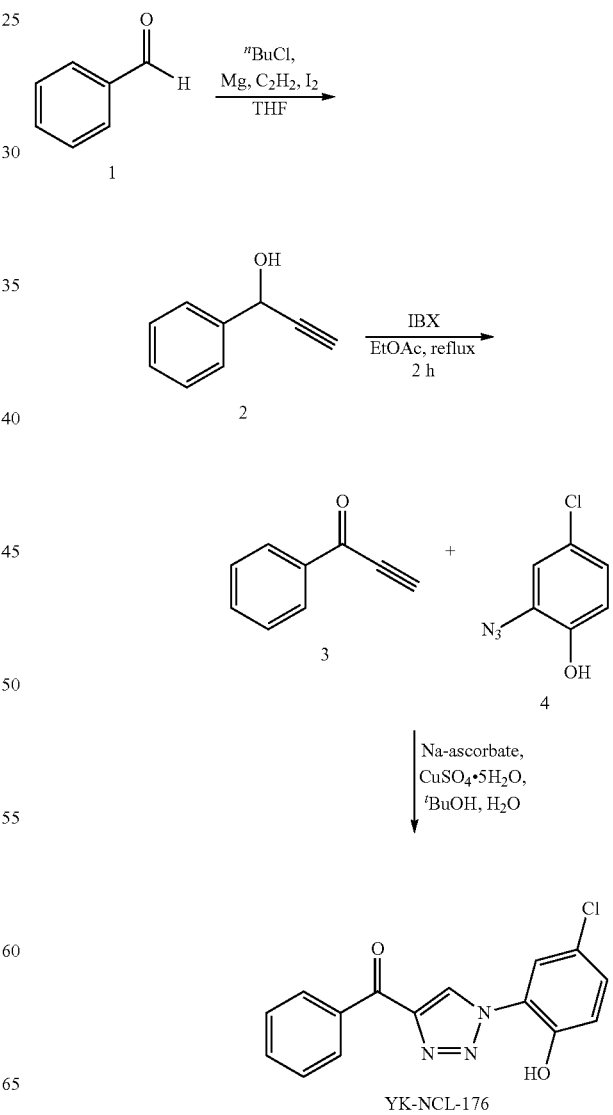

Alkyne 2 (120 mg, 0.922 mmol) and azidophenol 4 (156 mg, 0.922 mmol) were suspended in 12 mL of a 1:3 water/tert-butanol mixture. Sodium ascorbate (0.876 mmol) was added, followed by copper(II) sulfate pentahydrate (29 mg, 0.184 mmol). The heterogeneous mixture was stirred vigorously over 10 min, at which point it cleared and TLC analysis indicated complete consumption of the reactants. The reaction mixture was extracted with ethylacetate, dried on $Na_2SO_4$ and purified by column chromatography. The pure product (YK-NCL-176) was obtained as an off-white powder 253 mg (92%); m.p 211° C.; $^1$H NMR (200 MHz, CHLOROFORM-d) δ ppm 7.07 (d, J=8.3 Hz, 1H), 7.32 (d, J=8.3 Hz, 1H), 7.57-7.64 (m, 3H), 7.89 (br s, 1H), 8.31 (d, J=5.7 Hz, 2H), 9.07 (br s, 1H); $^{13}$C NMR (125 MHz, CHLOROFORM-d) δ ppm 117.3 (d), 123.0 (d), 123.5 (s), 127.3 (d, 2C), 129.1 (d, 3C), 129.3 (d), 132.3 (d), 135.7 (s), 145.8 (s), 147.1 (s, 2C), 184.7 (s).

Example 2. 2,2'-(4,4'-(hydroxy(phenyl)methylene)bis(1H-1,2,3-triazole-4,1-diyl))bis(4-chlorophenol) (YK-NCL-179)

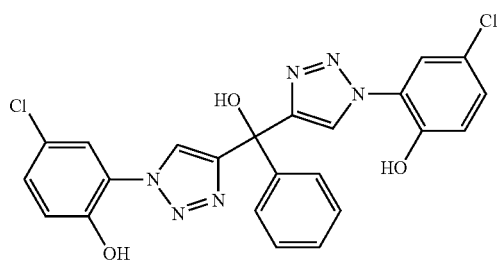

YK-NCL-179 (NCL-179) was synthesized as shown in Scheme 2.

Example 3. (3,5-Bis(trifluoromethyl)phenyl)(1-(5-chloro-2-hydroxyphenyl)-1H-1,2,3-triazol-4-yl)methanone (YK-NCl-240)

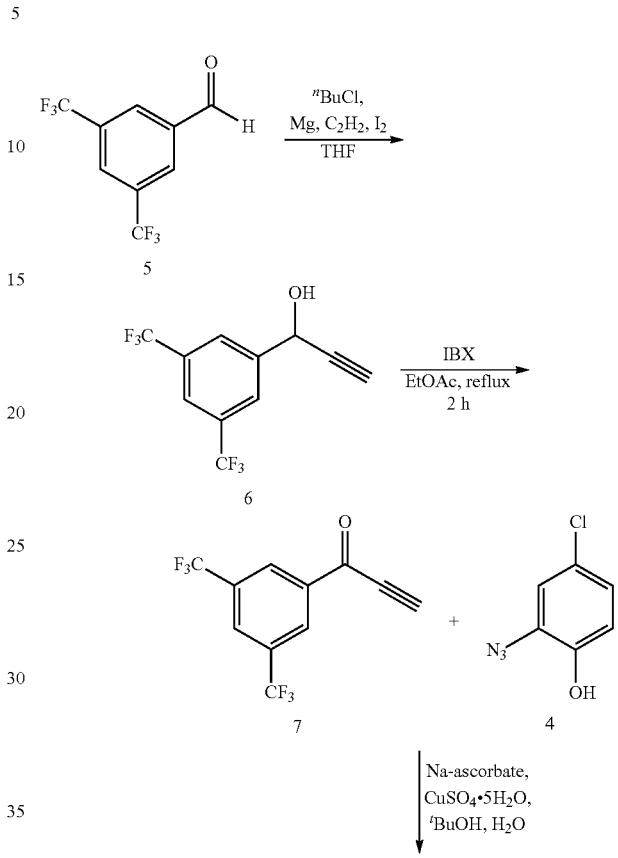

Scheme 2

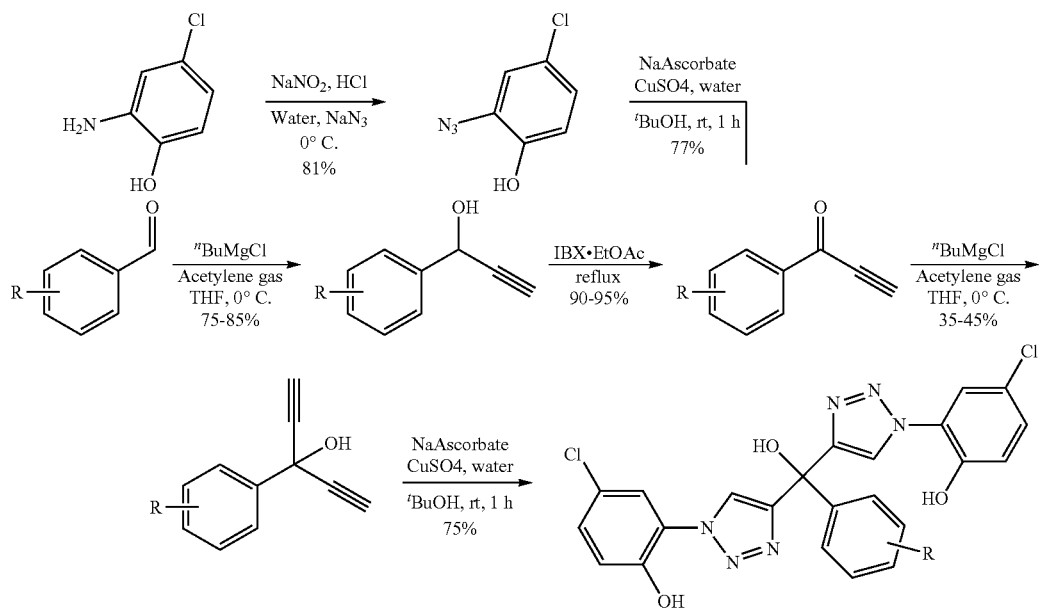

R = H (YK-NCL-179)

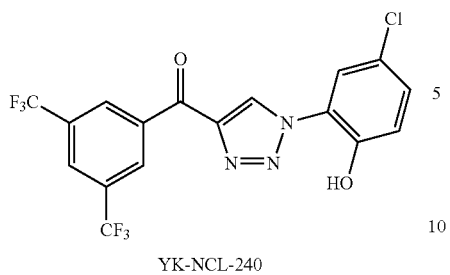

YK-NCL-240

Alkyne 7 (500 mg, 1.879 mmol) and azidophenol 4 (319 mg, 1.879 mmol) were suspended in 12 mL of a 1:3 water/tert-butanol mixture. Sodium ascorbate (1.786 mmol) was added, followed by copper(II) sulfate pentahydrate (60 mg, 0.376 mmol). The heterogeneous mixture was stirred vigorously over 10 min, at which point it cleared and TLC analysis indicated complete consumption of the reactants. The reaction mixture was extracted with ethylacetate, dried (Na$_2$SO$_4$) and purified by column chromatography. The pure product (YK-NCL-240) was obtained as an off-white powder 728 mg (89%); $^1$H NMR (500 MHz, CHLOROFORM-d) δ ppm 7.08 (d, J=8.9 Hz, 1H), 7.32 (dd, J=2.4, 8.9 Hz, 1H), 7.94 (d, J=2.4 Hz, 1H), 8.17 (br s, 1H), 8.99 (br s, 2H), 9.22 (s, 1H); $^{13}$C NMR (125 MHz, CHLOROFORM-d) δ ppm 118.0 (d), 119.5 (s), 121.6 (s), 123.6 (d, 2C), 123.9 (s, d, J=23.6 Hz), 124.4 (s), 126.0 (d, qt, J=3.6 Hz), 130.1 (d, 2C), 130.4 (d, J=2.7 Hz), 130.5 (d), 131.7 (s, q, J=33.6 Hz, 2C), 137.8 (s), 146.1 (s), 147.5 (s), 182.5 (s); HRMS(ESI) calcd for C$_{17}$H$_9$O$_2$N$_3$ClF$_6$ (M$^+$+H): 436.0282. found: 436.0289.

Example 4. 2,2'-(((3,5-Bis(trifluoromethyl)phenyl) (hydroxy)methylene)bis(1H-1,2,3-triazole-4,1-diyl)) bis(4-chlorophenol) (YK-NCL-198)

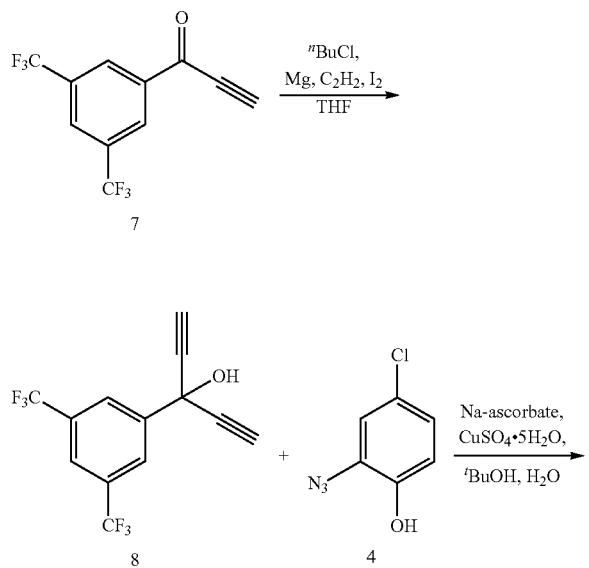

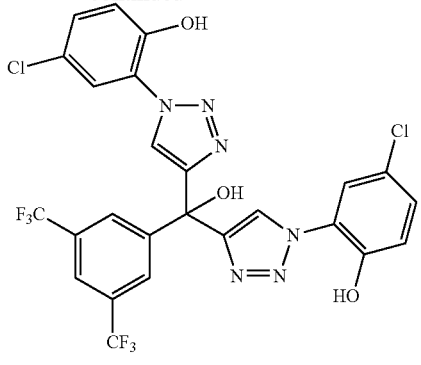

YK-NCL-198

Alkyne 8 (60 mg, 0.205 mmol) and azidophenol 4 (69 mg, 0.411 mmol) were suspended in 12 mL of a 1:3 water/tert-butanol mixture. Sodium ascorbate (38 mg, 0.195 mmol) was added, followed by copper(II) sulfate pentahydrate (6 mg, 0.041 mmol). The heterogeneous mixture was stirred vigorously over 10 min, at which point it cleared and TLC analysis indicated complete consumption of the reactants. The reaction mixture was extracted with ethylacetate, dried on Na$_2$SO$_4$ and purified by column chromatography. The pure product (YK-NCL-198) was obtained as an off-white powder 97 mg (75%); m.p 214° C.; $^1$H NMR (200 MHz, CHLOROFORM-d) δ ppm 6.81 (d, J=8.8 Hz, 2H), 7.05 (dd, J=2.5, 8.9 Hz, 2H), 7.56 (d, J=2.5 Hz, 2H), 7.64 (br s, 1H), 8.08 (br s, 2H), 8.23 (s, 2H); $^{13}$C NMR (50 MHz, CHLOROFORM-d) δ ppm 70.9 (s), 118.1 (s, 2C), 118.1 (d, 4C), 121.2 (d), 123.7 (d, 2C), 124.1 (s, 2C), 124.2 (d, J=2.9 Hz), 124.5 (s), 126.7 (d, J=2.3 Hz), 129.5 (d, 2C), 131.0 (s, J=33.7 Hz, 2C), 131.3 (s), 146.9 (s), 147.6 (s, 2C), 151.5 (s, 2C); HRMS(ESI) calcd for C$_{25}$H$_{15}$O$_3$N$_6$Cl$_2$F$_6$ (M$^+$+H): 631.0481. found: 631.0482.

Example 5. In Vitro Cell Viability of Cancer Cells

Figure 2:
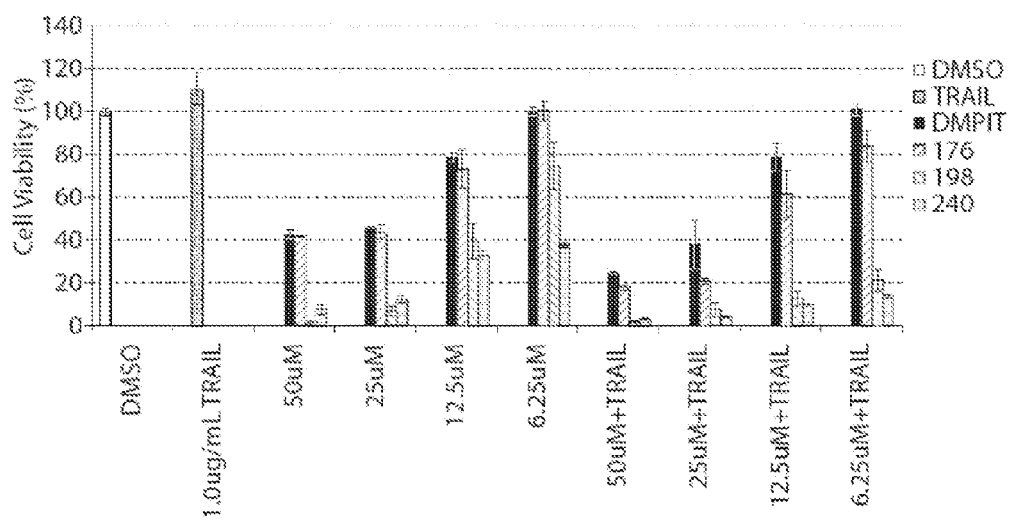
FIG. 2 is a graph depicting cell viability in A2780 human ovarian cancer cells following incubation for 24 h in the presence of DMSO, TRAIL, DM-PIT-1 (DMPIT), NCL-176 (176), NCL-198 (198), and NCL-240 (240) at the concentrations shown.

A2780 human ovarian cancer cells were maintained in culture at 37° C., 5% CO$_2$, complete medium for 24 h in the presence of various final concentrations of DM-PIT-1, YK-NCL-176, YK-NCL-198, or NK-YCL-240, each in DMSO, with or without 1 μg/mL TRAIL. DMSO alone was used as a negative control. Following the incubation, cell viability was measured using an ATP assay. Results are shown in FIG. 2. As shown in FIG. 2, DM-PIT-1, YK-NCL-176, YK-NCL-198, and NK-YCL-240 alone significantly reduced cell viability by at least 50 percent at concentrations of 25 μM, 25 μM, 12.5 μM, and <6.25 μM, respectively, while TRAIL alone had essentially no effect on cell viability. Surprisingly, DM-PIT-1, YK-NCL-176, YK-NCL-198, and NK-YCL-240, each in combination with TRAIL, further reduced cell viability. Compared to DM-PIT-1 alone, the EC$_{50}$ value for YK-NCL-240 alone was improved 15-fold, while compared to the combination of DM-PIT-1 and TRAIL, the EC$_{50}$ value for the combination of YK-NCL-240 and TRAIL was improved 20-fold. See Table 1.

TABLE 1

Comparison of EC$_{50}$ values

| Compound | EC$_{50}$ (μM) alone | EC$_{50}$ (μM) with TRAIL |
|---|---|---|
| DM-PIT-1 | 30.48 | 18.71 |
| NCL-240 | 1.85 | 1.11 |

Figure 3A:
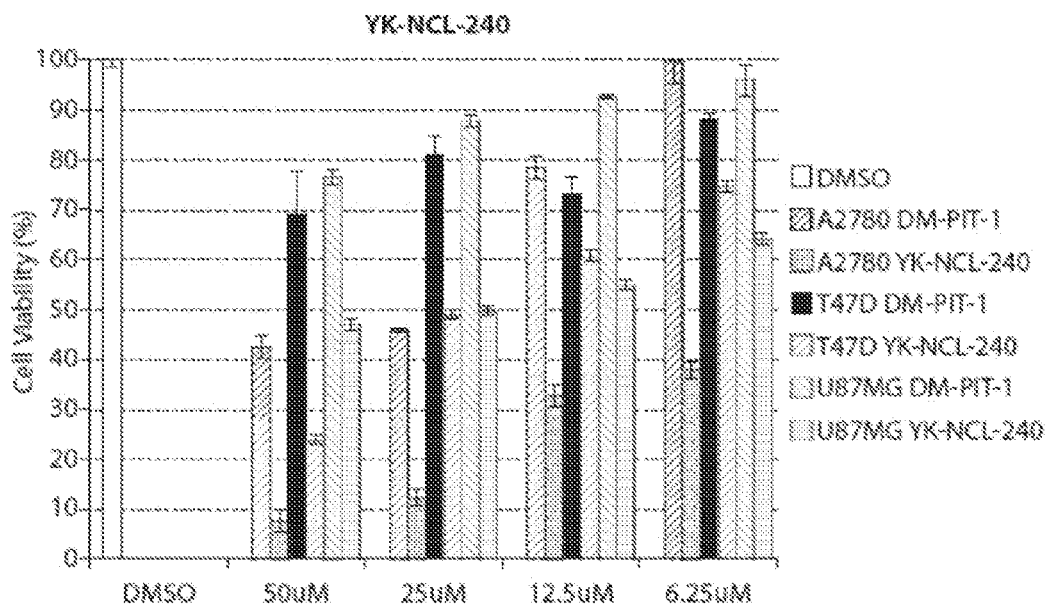
FIG. 3 is a pair of graphs depicting cell viability of A2780 human ovarian cancer cells, U87MG human glioblastoma cells, T47D human breast cancer cells, and DU145 human prostated cancer cells following incubation for 24 h in the presence of (A) DMSO, DM-PIT-1, and YK-NCL-240, at the concentrations shown, each alone, and (B) YK-NCL-240, at the concentrations shown, in combination with 1 μg/mL TRAIL.
Figure 3B:
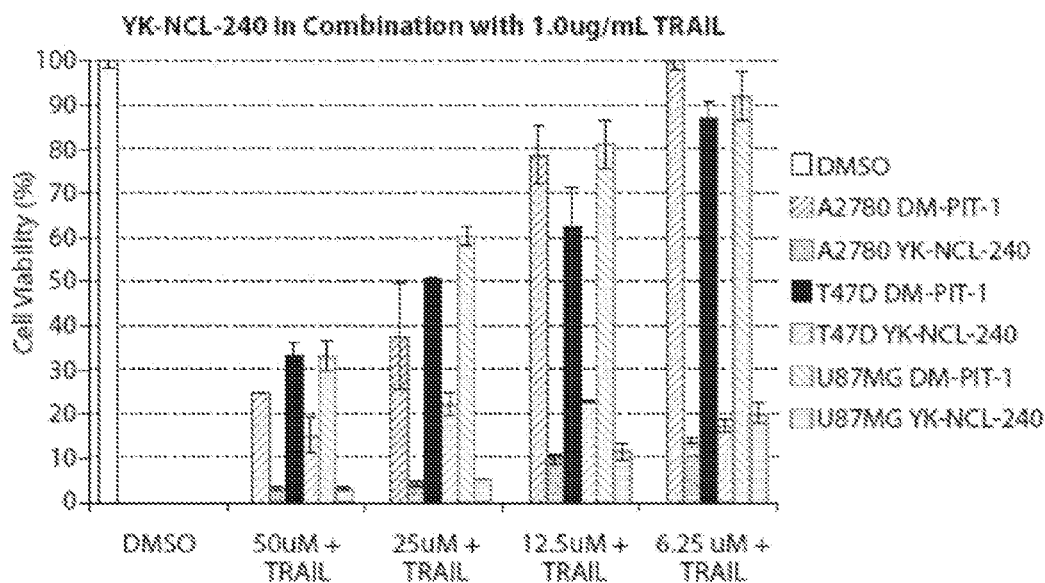

Using similar methods, NK-YCL-240, again in DMSO, was found to reduce in vitro cell viability in a variety of human cancer cell lines: U87MG human glioblastoma cells, T47D human breast cancer cells, and DU145 human prostate cancer cells. Combination with TRAIL again exhibited a synergistic effect. See FIG. 3.

Example 6. In Vitro Cell Viability of Cancer Cells

A2780 human ovarian cancer cells were maintained in culture at 37° C., 5% $CO_2$, complete medium for 24 h in the presence of various final concentrations of DM-PIT-1, YK-NCL-217, YK-NCL-218, NK-YCL-219, YK-NCL-220, YK-NCL-234, or YK-NCL-241, each in DMSO, with or without 1 μg/mL TRAIL. DMSO alone was used as a negative control. Following the incubation, cell viability was measured using an ATP assay. Results are shown in Table 2.

TABLE 2

Comparison of $EC_{50}$ values against A2780 human ovarian cancer cells

| Compound | ID | $EC_{50}$ (μM) alone | $EC_{50}$ (μM) with TRAIL |
|---|---|---|---|
| [structure] | YK-NCL-217 | 50.9 | 13.5 |
| [structure] | YK-NCL-218 | >100 | 22.8 |
| [structure] | YK-NCL-219 | 24.1 | 9.2 |

TABLE 2-continued

Comparison of EC$_{50}$ values against A2780 human ovarian cancer cells

| Compound | ID | EC$_{50}$ (μM) alone | EC$_{50}$ (μM) with TRAIL |
|---|---|---|---|
| (structure) | YK-NCL-220 | >100 | 16.9 |
| (structure) | YK-NCL-234 | 16.2 | 14.0 |
| (structure) | YK-NCL-241 | >100 | >100 |

Example 7. In Vitro Cell Viability of Cancer Cells

U87MG human glioblastoma cells were maintained in culture at 37° C., 5% CO$_2$, complete medium for 24 h in the presence of various final concentrations of YK-NCL-176, YK-NCL-177, YK-NCL-178, YK-NCL-179, YK-NCL-180, YK-NCL-183, YK-NCL-184, YK-NCL-185, YK-NCL-186, YK-NCL-187, YK-NCL-188, YK-NCL-189, YK-NCL-190, YK-NCL-191, YK-NCL-192, YK-NCL-193, YK-NCL-194, YK-NCL-195, YK-NCL-196, YK-NCL-197, NK-YCL-198, or YK-NCL-199, each in DMSO, with or without 1 μg/mL TRAIL. DMSO alone was used as a negative control. Following the incubation, cell viability was measured using an ATP assay. Results are shown in Table 3.

TABLE 3

Comparison of EC$_{50}$ values against U87MG human glioblastoma cells

| Compound | ID | EC$_{50}$ (μM) alone | EC$_{50}$ (μM) with TRAIL |
|---|---|---|---|
| (structure) | YK-NCL-176 | 103.6 | 51.6 |

TABLE 3-continued

Comparison of EC$_{50}$ values against U87MG human glioblastoma cells

| Compound | ID | EC$_{50}$ (μM) alone | EC$_{50}$ (μM) with TRAIL |
|---|---|---|---|
| (structure) | YK-NCL-177 | >100 | >100 |
| (structure) | YK-NCL-178 | >100 | >100 |
| (structure) | YK-NCL-179 | 36.7 | 20.4 |
| (structure) | YK-NCL-180 | >100 | >100 |
| (structure) | YK-NCL-183 | >100 | 64.4 |
| (structure) | YK-NCL-184 | >100 | >100 |

TABLE 3-continued

Comparison of EC$_{50}$ values against U87MG human glioblastoma cells

| Compound | ID | EC$_{50}$ (µM) alone | EC$_{50}$ (µM) with TRAIL |
|---|---|---|---|
|  | YK-NCL-185 | 8.1 | 8.0 |
|  | YK-NCL-186 | >100 | >100 |
|  | YK-NCL-187 | 85.2 | 74.9 |
|  | YK-NCL-188 | >100 | >100 |
|  | YK-NCL-189 | >100 | >100 |
|  | YK-NCL-190 | 57.8 | 30.6 |
|  | YK-NCL-191 | 48.9 | 42.3 |

TABLE 3-continued
Comparison of EC$_{50}$ values against U87MG human glioblastoma cells
| Compound | ID | EC$_{50}$ (μM) alone | EC$_{50}$ (μM) with TRAIL |
|---|---|---|---|
| 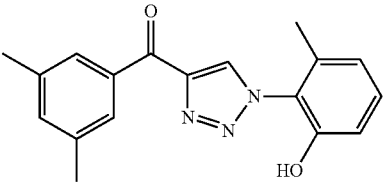 [SMILES: Cc1cc(C)cc(C(=O)c2cn(-c3c(C)cccc3O)nn2)c1] | YK-NCL-192 | 104.0 | 98.4 |
| 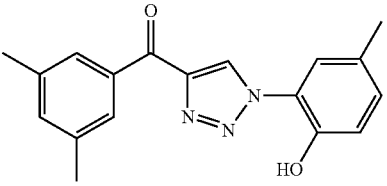 | YK-NCL-193 | >100 | >100 |
| 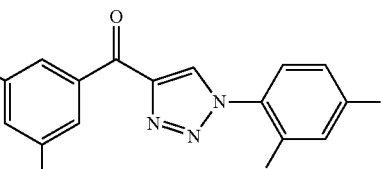 | YK-NCL-194 | 89.1 | 70.5 |
| 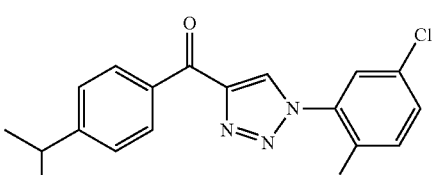 | YK-NCL-195 | 64.1 | 41.6 |
| 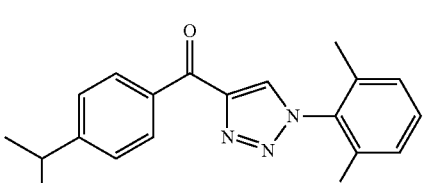 | YK-NCL-196 | >100 | >100 |
| 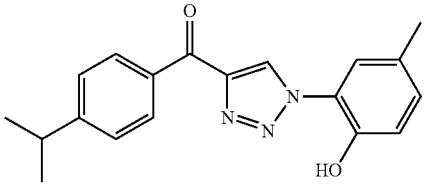 [SMILES: Cc1ccc(O)c(-n2cc(C(=O)c3ccc(C(C)C)cc3)nn2)c1] | YK-NCL-197 | >100 | >100 |

TABLE 3-continued

Comparison of EC$_{50}$ values against U87MG human glioblastoma cells

| Compound | ID | EC$_{50}$ (µM) alone | EC$_{50}$ (µM) with TRAIL |
|---|---|---|---|
| *(structure)* | NK-YCL-198 | 34.8 | 18.8 |
| *(structure)* | YK-NCL-199 | >100 | 95.3 |

Example 8. In Vitro Inhibition of Cellular Migration by YK-NCL-240

A2780 cells and T47D cells were grown to confluence in separate cultures under conditions of 37° C., 5% CO$_2$, and complete medium. At time zero, a pipette tip was dragged across the cells, producing a linear defect in the confluent layer of cells. Medium was then supplemented with various concentrations of DM-PIT-1, YK-NCL-176, or YK-NCL-240, or an equivalent volume of DMSO alone, and cells were maintained in culture for an additional 76 h. Linear defects were viewed with a microscope at 0, 21, 47, 69, and 76 h following addition of test agent, and the width of the defect was quantitated at each time point. This in vitro assay represents a model of wound closure. Results are shown in FIG. 4.

Figure 4A:
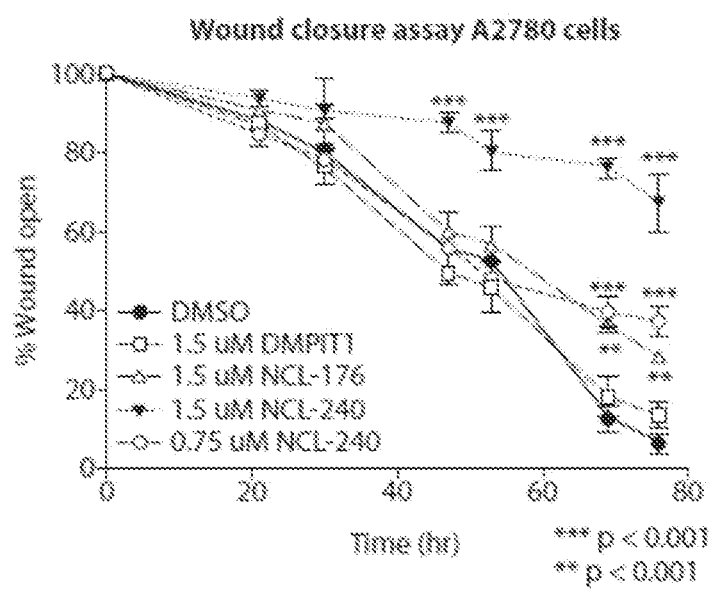
FIG. 4 is a pair of graphs depicting wound closure for (A) A2780 human ovarian cancer cells and (B) T47D human breast cancer cells, each in the presence of DMSO or the indicated concentrations of DM-PIT-1, YK-NCL-176, and YK-NCL-240.
Figure 4B:
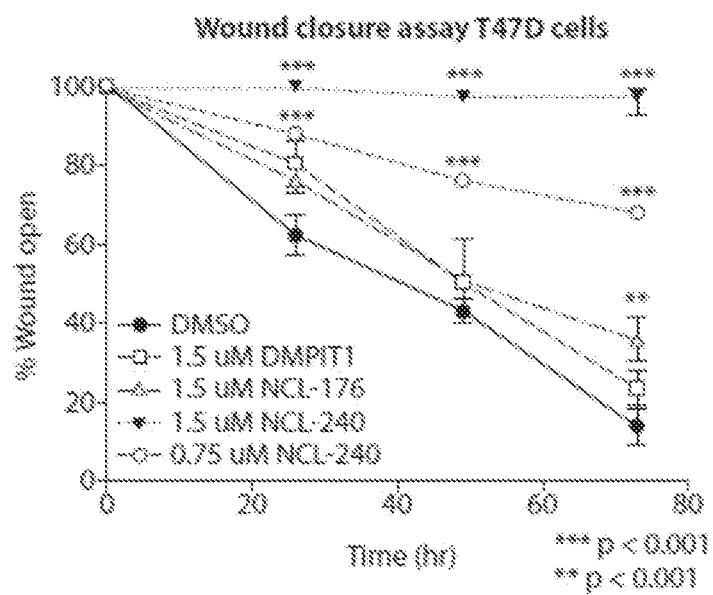

As is evident from FIG. 4A, YK-NCL-240 inhibited cell migration in vitro significantly more effectively than either DM-PIT-1 or YK-NCL-176, while YK-NCL-176 inhibited cell migration in vitro significantly more effectively than DM-PIT-1.

Similar inhibition of cellular migration by YK-NCL-240 was also shown in T47D, U87MG, and DU145 cells. See, for example, FIG. 4B.

This ability to inhibit cellular migration may translate into inhibition of angiogenesis within tumors as well as inhibition of metastasis.

Example 9. Improved Inhibition of PH Domain Binding to PIP3

Figure 5:
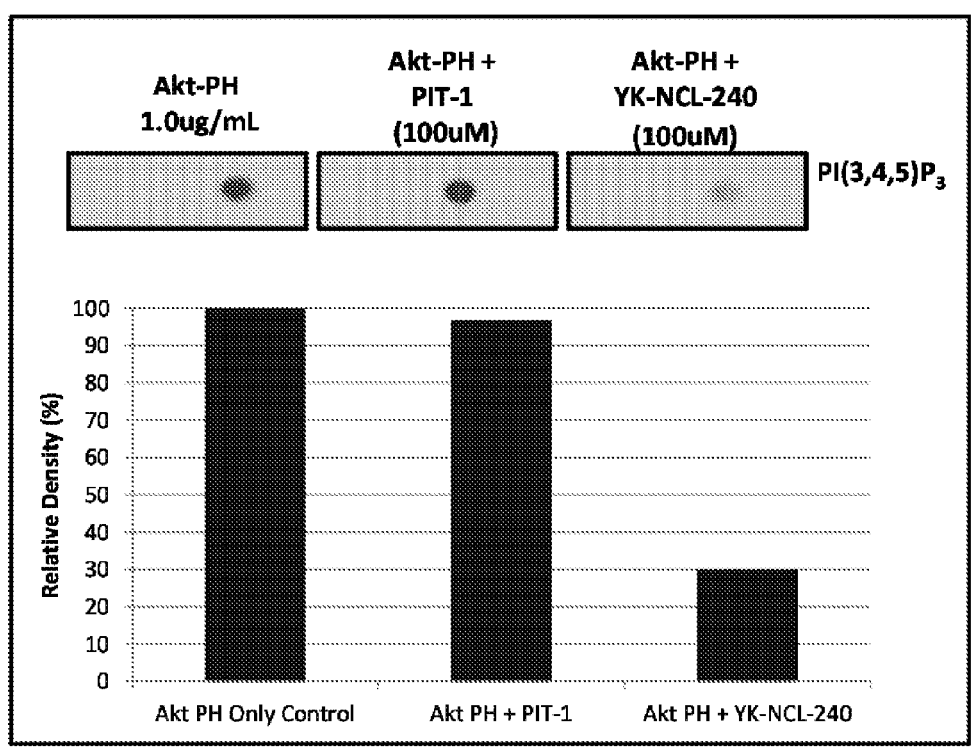
FIG. 5 is a graph depicting inhibition of Akt PH domain binding to PIP3 in the presence of DMSO or the indicated concentrations of DM-PIT-1 and YK-NCL-240.

FIG. 5 demonstrates that the binding of the Akt PH domain to PIP3 in vitro is robustly inhibited by the addition of YK-NCL-240. The effect of YK-NCL-240 is significantly improved compared to DM-PIT-1 in the same assay.

Example 10. Drug-Loaded and Surface-Modified Micelles

Materials 1,2-Distearoyl-sn-glycero-3-phosphoethanolamine-N-[methoxy(polyethylene glycol)-2000] (PEG$_{2000}$-DSPE) and 1,2-dioleoyl-sn-glycero-3-phosphoethanolamine (DOPE) were purchased from Avanti Polar Lipids Inc (Alabaster, Ala.) and used without further purification. pNP-PEG$_{3400}$-pNP was purchased from Laysan Bio (Arab, Ala.). Recombinant His6-tagged human TRAIL was produced in *E. coli* and purified using Ni$^{2+}$ chromatography as previously described. Pan G et al., *Science* 276:111-113 (1997); Pan G et al., *Science* 277:815-818 (1997). The bacterial expression vector was a generous gift of Dr V. Dixit (Genentech).

DM-PIT-1 and the novel analogs NCL-176, NCL-179, NCL-198 and NCL-240 (FIG. 1) were synthesized at the National Chemical Laboratory (Pune, India). BCA kits for determining protein concentrations were purchased from Pierce (Rockford, Ill.). Spectra/Pro® regenerated cellulose dialysis membrane were purchased from Spectrum Laboratories Inc. (USA).

Micelle Preparation

Drug-loaded micelles were prepared by the thin-film hydration method. Sawant R R et al., *Methods Mol Biol* 624:131-149 (2010). Briefly, PEG$_{2000}$-DSPE dissolved in chloroform was added to round bottom flasks. Various weight % of drug dissolved in acetonitrile was added and the sample was vortexed for complete mixing. Organic solvents were then evaporated under a rotary evaporator to form a thin film. Films were further dried by freeze-drying on a Freezone 4.5 Freeze Dry System (Labconco, Kansas City, Mo.) for at least 4 hours. Films were rehydrated with 1×PBS pH 7.4 to a lipid concentration of 13.07 mg/mL and vortexed for at least 5 minutes to allow for complete lipid dissolution and micelle formation. Drug-loaded micelles were then centrifuged at 14,000 rpm for 5 minutes to precipitate any unincorporated drug and further filtered using a 0.2 µm filter (Nalgene, Rochester, N.Y.).

Drug incorporation efficiency was measured by reverse phase HPLC using an Xbridge $C_{18}$ (2.1 cm×250 cm) column (Waters Corporation, Milford, Mass.) on a Hitachi Elite LaChrom HPLC with autosampler (Pleasanton, Calif.). The HPLC method was modified from previously published method. Skidan I et al., *J Chromatogr B Analyt Technol Biomed Life Sci* 879:1610-1616 (2011). The mobile phase consisted of either 70:30 acetonitrile:water (DM-PIT-1) or 60:40 acetonitrile:water (NCL-176, NCL-179, NCL-198, NCL-240) with a flow rate of 1 mL/min. Detection of drug was performed at a wavelength corresponding to a peak on the absorption spectrum (DM-PIT-1: 320 nm, NCL-176: 260 nm, NCL-179: 295 nm, NCL-198: 295 nm, NCL-240: 300 nm). Sample injections were kept constant at 50 µL and the sample runtime was 10 min. Concentration of drug was determined by measuring the area under curve of the peak. Standard curves of stock drug in acetonitrile from concentrations of 10 µg/mL to 15 ng/mL were used to determine incorporation of drug in micelles. 5 µL of dialyzed drug-loaded micelles were diluted in 495 µL acetonitrile to destroy micelles.

All micellar samples were measured for their size distribution and zeta-potential using the Zetaplus (Brookhaven Instruments Corporation, Holtsville, N.Y., USA). Briefly, 50 µL of micelle sample was dissolved in 1 mL of distilled water, and micelle size and zeta-potential were analyzed according to manufacturer's protocol.

Micellar Drug Release

Drug-loaded micelles were analyzed for their in vitro drug release profile at 37° C. in 1×PBS pH 7.4 over 48 hrs. Micelles were prepared as described previously. 500 µL of drug-loaded micelles were aliquoted into Spectra/Pro® regenerated cellulose dialysis membranes with a MWCO of 1,000 Da and dialyzed against a large excess of 1×PBS pH 7.4. At predetermined times, dialysis bags were opened and aliquots of sample were taken and diluted with 200 µL acetonitrile. Drug concentration was determined by HPLC using previously described methods.

Synthesis of pNP-$PEG_{3400}$-PE pNP-$PEG_{3400}$-PE was synthesized according to standardized in-lab procedures. Sawant R R et al., *Methods Mol Biol* 751:357-378 (2011). pNP-$PEG_{3400}$-pNP (Laysan Bio, Arab, Ala.) was dissolved in dry chloroform. DOPE in chloroform was added, followed by triethylamine and reaction mixture was left overnight at room temperature under nitrogen with stirring. Solvents were then removed by rotary evaporation and films were further dried on a Freezone 4.5 Freeze Dry System (Labconco, Kansas City, Mo., USA) for at least 4 hours to remove any residual solvents. The dried film was then rehydrated with 0.001 M HCl and separated on sepharose column. Fractions were collected and analyzed by thin-layer chromatography to confirm pNP-$PEG_{3400}$-PE product. Product-containing fractions were frozen, lyophilized, weighed, and reconstituted with chloroform to appropriate stock concentrations and stored at −80° C.

Formulation and Characterization of TRAIL-Modified Micelles

TRAIL micelles were prepared by the thin-film hydration method as described previously. Skidan I et al., *Drug Deliv* 16:45-51 (2009). Briefly, $PEG_{2000}$-DSPE dissolved in chloroform was added to round bottom flasks. 5% (by mole of DSPE-$PEG_{2000}$) pNP-$PEG_{3400}$-PE dissolved in chloroform was added and the sample vortexed for complete mixing. Chloroform was then evaporated under a rotary evaporator to form a thin film. Freeze-dried films were then rehydrated with stock TRAIL (0.9-1.36 mg/mL) at a 40:1 molar ratio of pNP-PEG-PE:TRAIL. 1×PBS pH 8.5 was added to achieve a final lipid concentration of 13.07 mg/mL and samples were vortexed for 5 min to allow for complete lipid dissolution and micelle formation. The pH of the solution was adjusted with 1.0 N NaOH to 8.5. Reaction proceeded for 4 h at room temperature to allow sufficient TRAIL conjugation and complete hydrolysis of unreacted pNP groups. TRAIL micelles were then dialyzed using a 100,000 molecular weight cutoff (MWCO) membrane against 1 L 1×PBS pH 7.4 for 1 h followed by another 4 h of dialysis in 1 L fresh 1×PBS pH 7.4.

Conjugation efficiency of TRAIL was measured using a micro BCA kit (Pierce, Rockford, Ill.) according to the provider's procedure. Protein content was determined by comparing TRAIL micelles to BCA standards. Signals from TRAIL samples were normalized with plain micelle samples at the same lipid concentration.

All micelle samples were measured for their size distribution and zeta potential using the Zetaplus (Brookhaven Instruments Corporation, Holtsville, N.Y., USA). Briefly, 50 µL of micelle sample was dissolved in 1 mL of distilled water and micelle size and zeta potential were analyzed according to manufacturer's protocol.

Figure 6:
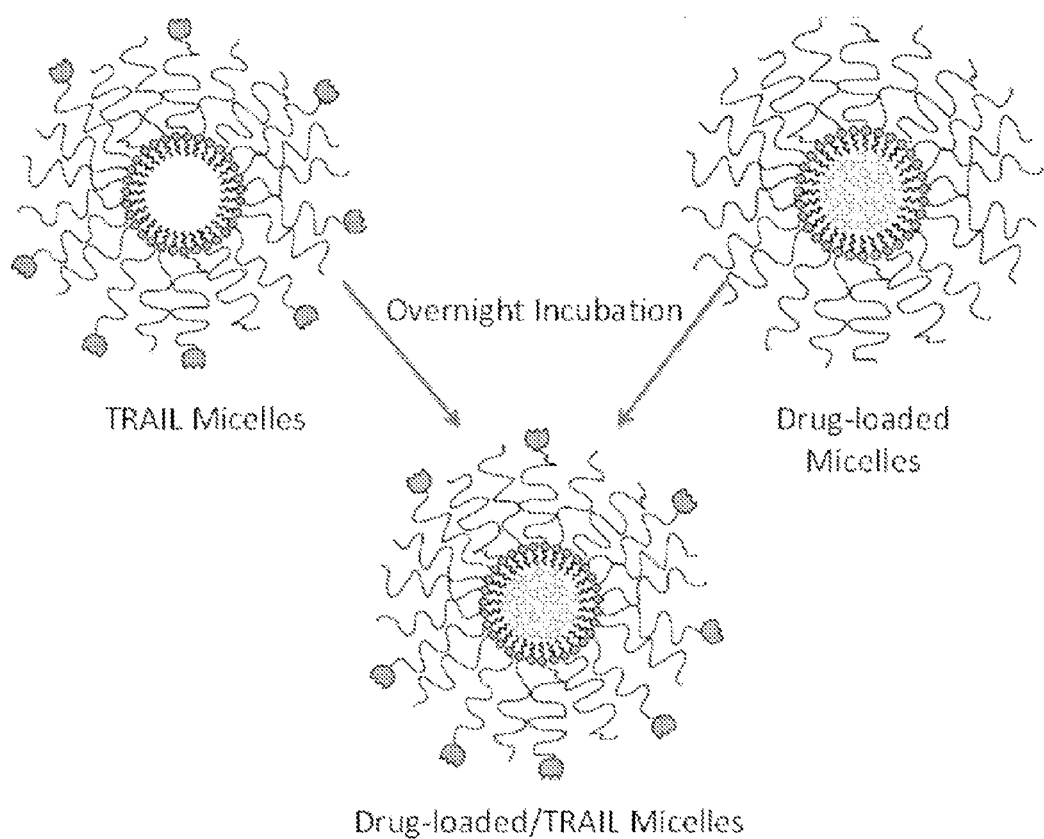
FIG. 6 depicts formulation of drug-loaded TRAIL-modified micelles.

Formulation and Characterization of Combination Drug-Loaded/TRAIL-Modified Micelles Micelles have been shown to rapidly exchange their component monomers with neighboring micelles, thereby forming a homogenous population. Reulen S W A et al., *Bioconjugate Chem* 21:860-866 (2010). Thus, mixing drug-loaded micelles with TRAIL-modified micelles was found to yield a single population of drug-loaded/TRAIL-modified micelles (FIG. 6). Sample aliquots were combined, vortexed, and allowed to mix for at least 4 hours at room temperature. Samples were measured for size distribution and zeta potential as previously described.

Statistical Analysis

Wherever possible, data was generated in triplicates for proper statistical analysis. In vitro experiments are reported as mean+/−standard deviation. One-way ANOVA followed by Tukey's multiple comparison test was performed with significance determined by a p-value <0.05. Tumor volumes and weights are reported as mean+/−standard deviation.

Results

Preparation and Characterization of Drug-Loaded Micelles

All micelle formulations were successfully prepared by the thin-film hydration method. Following rehydration and filtration, all drug-loaded micelles formed a single population of micelles with a size of ~17 nm and a zeta-potential of ~−2.0 mV. These values are consistent with successful $PEG_{2000}$-PE micelle formation. Sawant R R et al., *Methods Mol Biol* 624:131-139 (2010).

Reverse phase HPLC methods were optimized to determine the micellar drug loading of each analog. Freshly prepared micelles were centrifuged and filtered to remove any unincorporated drug and HPLC was performed to determine the drug concentration and loading efficiency. Table 6 provides a summary of the loading properties of the various analogs in PEG$_{2000}$-PE micelles. The wt % used was determined in part by the loading efficiency of each drug, and in part by the desire to have drug-loaded micelles at similar concentrations for side-by-side in vitro analysis. NCL-179, NCL-198 and NCL-240 have >90% loading efficiency under these conditions, likely due to their high lipophilicity (Table 4). DM-PIT-1 and NCL-176 have slightly lower loading due to their lower lipophilicity. These results demonstrate that micellar preparations are capable of efficiently incorporating sufficient drug for further studies.

A micellar drug release study was performed to evaluate the ability of the drug to be released from the micelle. Results shown in FIG. 7 indicate an initial rapid release of all micelle-loaded analogs. DM-PIT-1 and NCL-176 were both completely released from micelles at 10 h, while NCL-179 and NCL-198 micelles release only 40% of their payload after 48 h. 60% of NCL-240 was released from the micelles following 48 h. DM-PIT-1 and NCL-176 both have lower Log P values (Table 4) and are therefore more hydrophilic than NCL-179, NCL-198, and NCL-240, helping to explain the more rapid and complete release of drug from micelles.

Preparation and Characterization of TRAIL-Modified Micelles

TRAIL micelles were analyzed for their protein concentration as determined by the BCA assay. Following extensive dialysis against 1×PBS, TRAIL-modified micelles were incubated with BCA reagent.

TRAIL was attached to the surface of micelles using the well-established pNP-PEG-PE conjugation technique described previously. Under the reaction conditions employed, the efficiency of the TRAIL pNP-PEG-PE reaction was 92.4%+/−6.8% with a resulting TRAIL concentration of 271.0 μg/mL+/−23.8 μg/mL. The addition of TRAIL to PEG-PE micelles resulted in an increase in size and decrease in zeta-potential as indicated in Table 7. Dilution of these TRAIL-modified micelles with unmodified micelles resulted in a decrease in size and an increase in zeta-potential as the concentration of TRAIL on the micelles is reduced. The concentration of TRAIL on the micelles and the favorable physicochemical properties of TRAIL-modified micelles were sufficient for in vitro analysis.

Drug-Loaded/TRAIL-Modified Combination Micelles

Following preparation and characterization of drug-loaded micelles and TRAIL-modified micelles, combination formulations were prepared by co-incubating appropriate amounts of each micelle for at least 4 h at room temperature. Due to the lipid mixing that occurs between micelles in solution, a single population of drug-loaded/TRAIL-modified micelles was obtained. Mixing of the formulations did not appear to have any effects on the drug-loading properties of the micelles and resulted in a single population of micelles with a size of ~30 nm (Table 7).

TABLE 4

Physical properties of DM-PIT-1 and compounds of the invention

| Compound | MW (g) | LogP[a] |
| --- | --- | --- |
| DM-PIT-1 | 351.76 | 3.22 |
| NCL-176 | 299.71 | 3.34 |
| NCL-179 | 495.32 | 4.97 |
| NCL-198 | 631.31 | 6.82 |
| NCL-240 | 435.71 | 5.18 |

[a]Lipinski CA et al., Adv Drug Deliv Rev 46(1-3): 3-26 (2001).

TABLE 5

Size and zeta-potential characterization of empty and drug-loaded micelles[b]

| Formulation | Size (nm) | Zeta Potential (mV) |
| --- | --- | --- |
| PEG$_{2000}$-PE micelles | 17.5 ± 0.1 | −6.1 ± 1.4 |
| DM-PIT-1 micelles | 18.1 ± 0.5 | −1.4 ± 1.1 |
| NCL-176 micelles | 16.2 ± 0.7 | −3.6 ± 1.4 |
| NCL-179 micelles | 16.0 ± 0.8 | −1.8 ± 0.6 |
| NCL-198 micelles | 16.4 ± 0.8 | −2.1 ± 0.7 |
| NCL-240 micelles | 17.4 ± 0.9 | −4.3 ± 0.8 |

[b]n = 3 with SD shown

TABLE 6

Drug Loading in PEG-PE micelles[c]

| Formulation | Drug/Lipid (Weight %) | Loading Eff. (%) | Drug Conc. in Micelles (μM) |
| --- | --- | --- | --- |
| DM-PIT-1 micelles | 4 | 66.6 ± 9.2 | 952.0 ± 96.2 |
| NCL-176 micelles | 3 | 70.7 ± 3.4 | 925.1 ± 113.1 |
| NCL-179 micelles | 5 | 95.8 ± 2.1 | 1125.0 ± 158.2 |
| NCL-198 micelles | 6 | 98..1 ± 3.0 | 1219.2 ± 37.9 |
| NCL-240 micelles | 4 | 90.3 ± 2.2 | 1553.8 ± 124.4 |

[c]PEG-PE concentration was constant at 13.07 mg/mL. Loading efficiency was determined by dividing the concentration of drug in micelles by the theoretical concentration. n = 3 with SD shown.

TABLE 7

Size and zeta-potential characterization of TRAIL-modified micelles[d]

| Formulation | Size (nm) | Zeta Potential (mV) |
| --- | --- | --- |
| PEG$_{2000}$-PE micelles | 17.5 ± 0.1 | −6.1 ± 1.4 |
| Freshly prepared concentrated TRAIL-modified micelles | 40.1 ± 3.1 | −20.3 ± 1.0 |
| Diluted (0.5 μg/mL) TRAIL-modified micelles | 27.2 ± 1.2 | −13.6 ± 0.6 |

[d]n = 3 with SD shown

Example 11. In Vitro Cell Viability Assay

Methods

Cell viability of A2780 ovarian carcinoma was measured using CellTiter-Blue® (Promega, Madison, Wis.) viability assay. Briefly, cells were seeded in 96-well plates according to proper cell densities (3,000-5,000 cells). After 24 h incubation in 5% CO$_2$ at 37° C., cells were treated with formulations at various concentrations for 24 h in serum complete media. After 24 h treatment, media was removed, the wells were washed with serum complete media and replaced with 50 μL media and 10 μL CellTiter-Blue®. Cell viability was evaluated after 4 h of incubation at 37° C. at 5% CO$_2$ by measuring the fluorescence (ex. 550 nm, em. 590 nm) using a Synergy HT multi-detection microplate reader (Biotek, Winooski, Vt.).

Results

Figure 7:
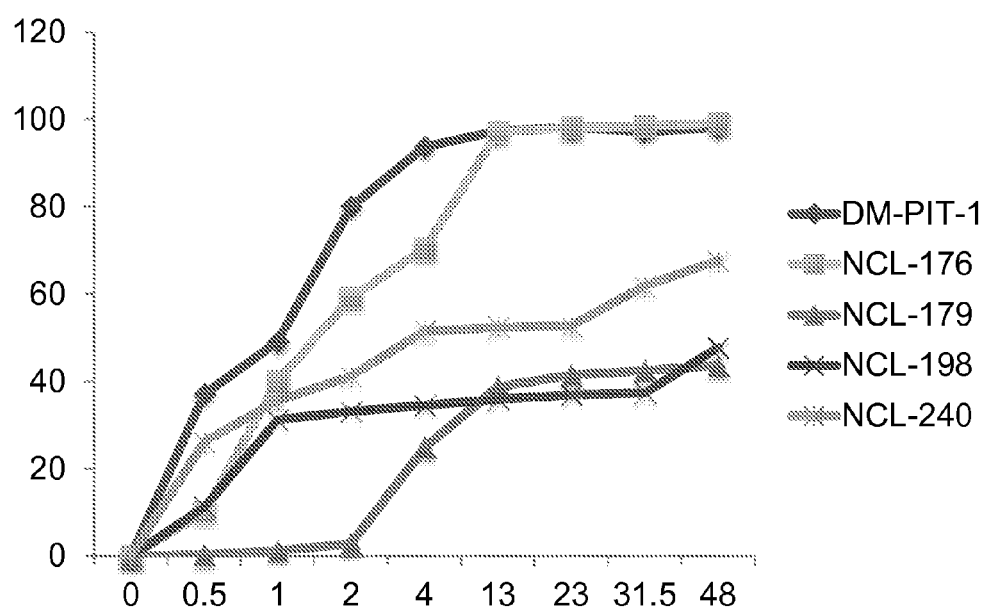
FIG. 7 is a graph depicting percentage of DM-PIT-1, YK-NCL-176, YK-NCL-179, YK-NCL-198, and YK-NCL-240 released from micelles at 37° C.
Figure 8A:
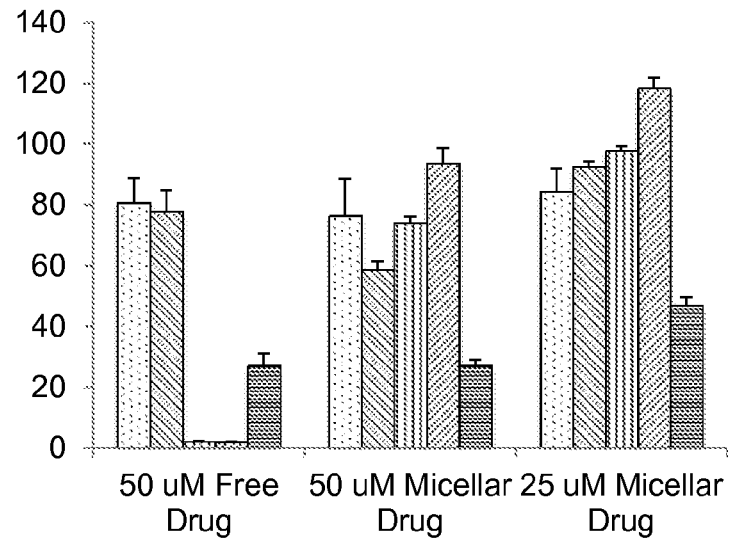
FIG. 8 is a pair of graphs depicting cell viability in A2780 human ovarian cancer cells following incubation for 24 h in the presence of (A) DM-PIT-1, YK-NCL-176, YK-NCL-179, YK-NCL-198, and YK-NCL-240 at the indicted concentrations and in the indicated formulations (all without TRAIL) or (B) TRAIL, DM-PIT-1, YK-NCL-176, YK-NCL-179, YK-NCL-198, and YK-NCL-240 at the indicted concentrations and in the indicated formulations. ***, $p<0.001$.

As shown in FIG. 8A, as compared to DM-PIT-1, the analogs NCL-179, NCL-198 and NCL-240 all possess improved cytotoxicity properties against A2780 when administered as free compound. However, following incorporation of the drug into micelles, the cytotoxic effects of NCL-179 and NCL-198 are abrogated. This is likely the result of poor micellar release of the drug as shown in FIG. 7. Increasing the incubation time of micellar NCL-179 and NCL-198 from 24 h to 72 h did not result in any additional cytotoxic effects. Conversely, micellar NCL-176 and especially NCL-240 had significantly improved cytotoxicity at 50 µM concentration versus DM-PIT-1, while micellar NCL-240 remained significantly more toxic at the 25 µM concentration.

Figure 8B:
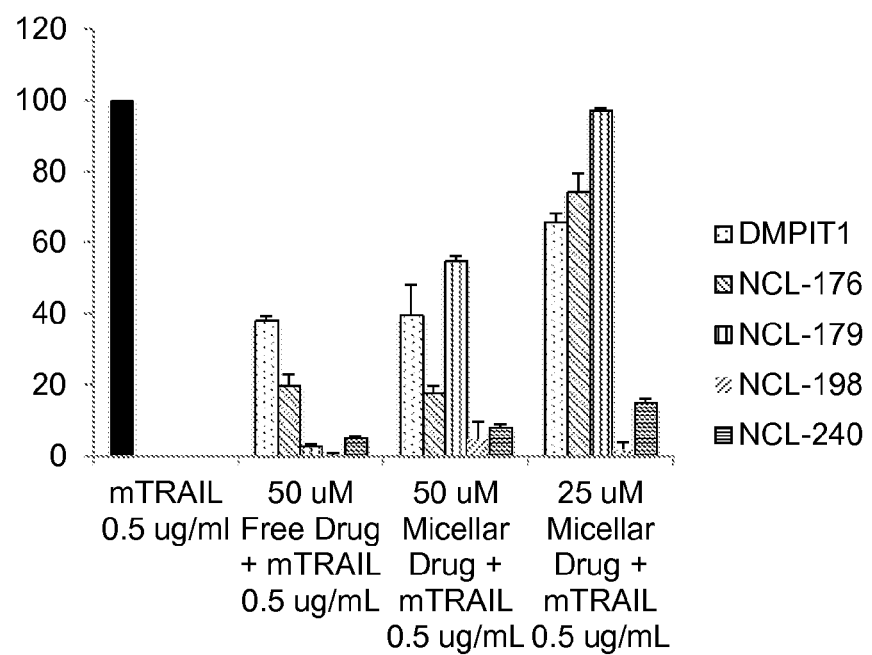

A2780 cells are resistant to TRAIL toxicity, and TRAIL micelles alone had no cytotoxic activity. Consistent with previous data showing synergy of DM-PIT-1 with TRAIL in TRAIL-resistant cell lines (Miao B et al., *Proc Natl Acad Sci USA* 107:20126-20131 (2010); Skidan I et al., *Drug Deliv* 16:45-51 (2009)), the addition of TRAIL to the NCL-176 and NCL-240 formulations resulted in a markedly increased cytotoxicity of formulations (FIG. 8B).

Example 12. In Vivo Tumor Inhibition by NCL-176

Methods
Tumor Response Study

Healthy female athymic nude mice (Nu$^-$/Nu$^-$) aged 6-8 weeks were purchased from Charles River Laboratories (Cambridge, Mass.). A2780 cells grown in culture were trypsinized and ~5×10$^6$ cells were suspended in 200 µL PBS. Cells were injected subcutaneously (s.c.) in the right flank of mice. Tumors were allowed to grow approximately 14 days and mice were randomized to treatment groups upon tumor reaching ~200 mm$^3$. All formulations were administered as daily intraperitoneal (i.p.) injections. The dose of drug was 5 mg/kg NCL-176 and 2.67 mg/kg TRAIL. Mice were monitored for changes in body weight and activity as indicators of toxicity. The tumors were measured daily using a vernier caliper (two perpendicular axes of the tumor were measured). Tumor volume was calculated according to the formula mm$^3$=½*(length×width). Following completion of the study, mice were euthanized and tumors were collected. Tumors were then weighed and stored in freezing media at −80° C. for further analysis.

Immunohistochemistry and TUNEL Assay

Immunohistochemistry assays were performed according to manufacturer's protocols. Briefly, frozen tumors were sectioned (8-µm), placed on slides, fixed with paraformaldehyde and air-dried. Subsequently, slides were incubated with blocking solution for 1 h followed by extensive washing and stained with either phospho-Akt (Ser-473) or cleaved caspase-3 (Asp 175) primary rabbit mAbs overnight at room temperature. Slides were extensively washed again and anti-rabbit Alexa Fluor® fluorescent secondary antibody was then incubated for 1 h followed by washing and mounting of coverslips. TUNEL assay was performed similar to the method above. However, following fixation of tissue, slides were permeabilized with proteinase K for 15 min at room temperature, and then subjected to TUNEL assay using the FragEl™ DNA fragmentation Detection Kit following the manufacturer's protocol. All slides were imaged by fluorescent microscopy, and random images were obtained from slides prepared from two different tumors per group.

Statistical Analysis

Wherever possible, data was generated in triplicates for proper statistical analysis. One-way ANOVA followed by Tukey's multiple comparison test was performed with significance determined by a p-value <0.05. Tumor volumes and weights are reported as mean+/−standard deviation.

Results

Figure 9:
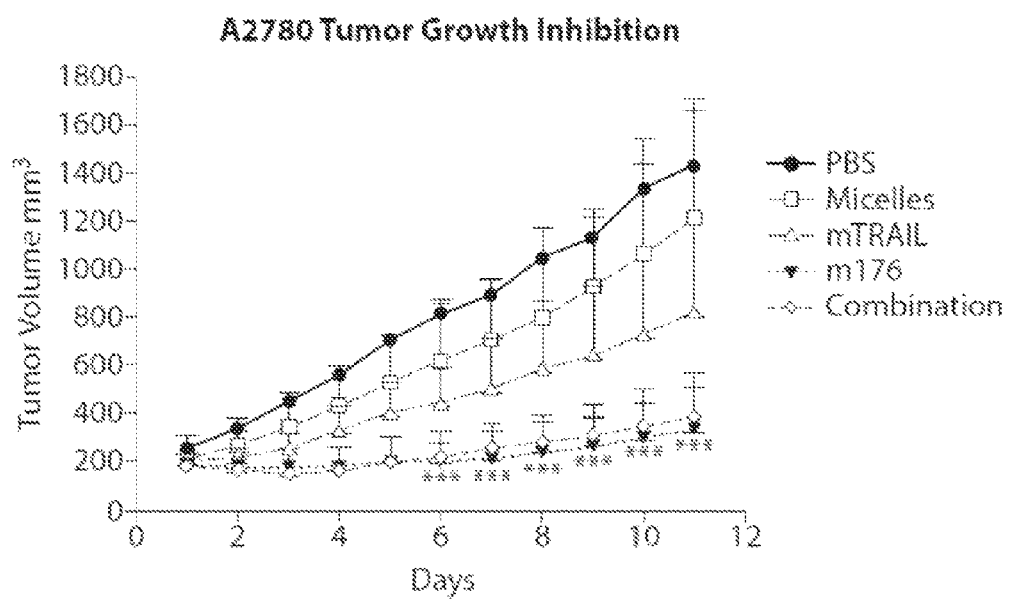
FIG. 9 is a graph depicting tumor volume of A2780 human ovarian carcinoma xenografts in mice treated with phosphate buffered saline (PBS), micelles alone (Micelles), micelles loaded with TRAIL (mTRAIL), micelles loaded with YK-NCL-176 (m176), and micelles loaded with both YK-NCL-176 and TRAIL (Combination). Values are expressed as mean tumor volume with error bars indicating SD (n=4). ***, $p<0.001$.

The tumor inhibition effect of micelle-loaded NCL-176 (m176) was tested in female nude mice bearing subcutaneous A2780 tumors alone and in combination with TRAIL (FIG. 9). Both the m176 and Combination formulations were able to significantly inhibit the growth of tumors with a 76.5% and 72.9% reduction in tumor volume as compared to controls. All formulations were well tolerated by the mice, with no signs of weight loss or overt toxicity. The limited effect of TRAIL addition on xenograft growth could be explained by the sub-optimal NCL-176/TRAIL ratio and/or the low overall close (2.67 mg/kg) as TRAIL was typically given at closes of 5 to 15 mg/kg in other xenograft studies. Ganapathy S et al., *PLoS One* 5:e15627 (2010); Ding W et al., *Cancer Lett* 293:158-166 (2010).

Tumor histology of harvested tumors confirmed the activity of NCL-176 and TRAIL in vivo. TUNEL staining was obvious in the m176 group and most pronounced in the combination group, indicating significant induction of apoptosis. Additionally, cleaved caspase-3 signal was most pronounced in the combination group, confirming activation of apoptotic signaling. Phospho-Akt (p473) staining was decreased in NCL-176 containing groups, demonstrating the efficacy of the drug at preventing Akt phosphorylation and activation. These results taken together indicate micellar NCL-176 alone and in combination with TRAIL can effectively inhibit tumor growth in vivo.

Example 13. In Vivo Tumor Inhibition by NCL-240

Methods
Tumor Response Study

Healthy female athymic nude mice (Nu$^-$/Nu$^-$) aged 6-8 weeks were purchased from Charles River Laboratories (Cambridge, Mass.). A2780 cells grown in culture were trypsinized and ~5×10$^6$ cells were suspended in 200 µL PBS. Cells were injected subcutaneously (s.c.) in the right flank of mice. Tumors were allowed to grow approximately 14 days and mice were randomized to treatment groups upon tumor reaching ~200 mm$^3$. All formulations were administered as daily intraperitoneal (i.p.) injections. The dose of drug was 20 mg/kg NCL-240 and 10 mg/kg TRAIL. Mice were monitored for changes in body weight and activity as indicators of toxicity. The tumors were measured daily using a vernier caliper (two perpendicular axes of the tumor were measured). Tumor volume was calculated according to the formula mm$^3$=½*(length×width). Following completion of the study, mice were euthanized and tumors were collected. Tumors were then weighed and stored in freezing media at −80° C. for further analysis.

Immunohistochemistry and TUNEL assay, as well as statistical analysis, were as described for Example 12.

Results

Figure 10A:
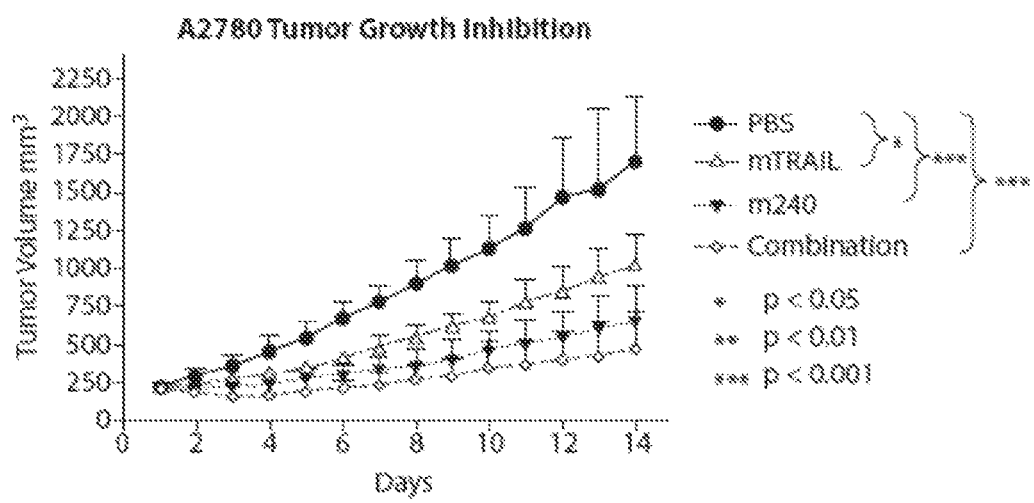
FIG. 10 is a pair of graphs depicting (A) tumor volume of A2780 human ovarian carcinoma xenografts in mice treated with phosphate buffered saline (PBS), micelles loaded with TRAIL (mTRAIL), micelles loaded with YK-NCL-240 (m240), and micelles loaded with both YK-NCL-240 and TRAIL (Combination), and (B) corresponding excised tumor weights. Values are expressed as means with error bars indicating SD (n=5). *, $p<0.05$; ***, $p<0.001$.
Figure 10B:
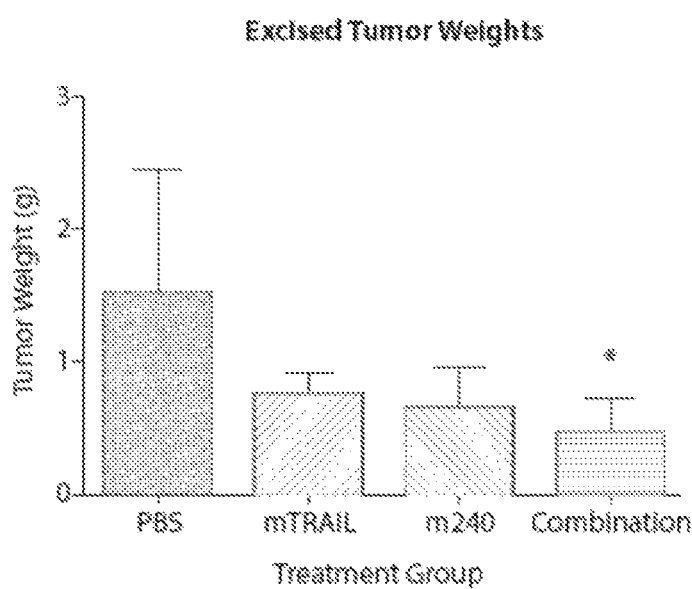

NCL-240 was also investigated for its tumor inhibition effects based on the fact that NCL-176 showed promising results. Because of the low efficacy seen with mTRAIL, the dose was increased to 10 mg/kg. Additionally, closes of up to 50 mg/kg of NCL-240 proved to be non-toxic in mice, so the dose of NCL-240 was also increased to 20 mg/kg. Micellar NCL-240 (m240) and combination micelles significantly (p<0.001) inhibited A2780 tumor growth in a subcutaneous mouse model (FIG. 10). Tumor growth was reduced by 63% in the m240 group while combination micelles inhibited growth 73% as compared to controls. The mTRAIL group also significantly inhibited tumor growth as compared to PBS (p<0.05). Additionally, the administration of the combination of TRAIL and NCL-240 resulted in significantly reduced tumor weight. These formulations were also found to be well tolerated in mice, as there was no apparent toxicity or loss of body weight.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

INCORPORATION BY REFERENCE

All patents and published patent applications mentioned in the description above are incorporated by reference herein in their entirety.

We claim:

1. A compound represented by formula (II), or a pharmaceutically acceptable salt thereof

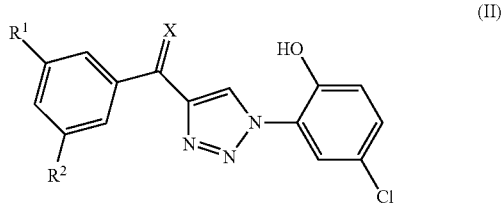

(II)

wherein:
$R^1$ represents methyl or —$CF_3$;
$R^2$ represents hydrogen, halogen, —OH, methyl, or —$CF_3$; and
X represents O or S.

2. The compound of claim 1, wherein X is O.
3. The compound of claim 1, wherein X is S.
4. The compound of claim 1, wherein $R^1$ is —$CF_3$.
5. The compound of claim 1, wherein each of $R^1$ and $R^2$ is —$CF_3$.
6. The compound represented by formula (III), or a pharmaceutically acceptable salt thereof

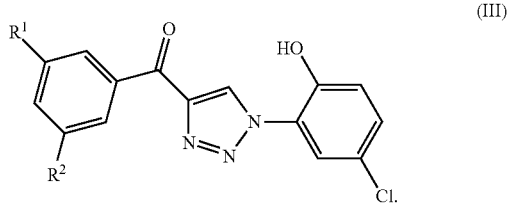

(III)

7. A compound represented by formula (V) or formula (VI), or a pharmaceutically acceptable salt thereof

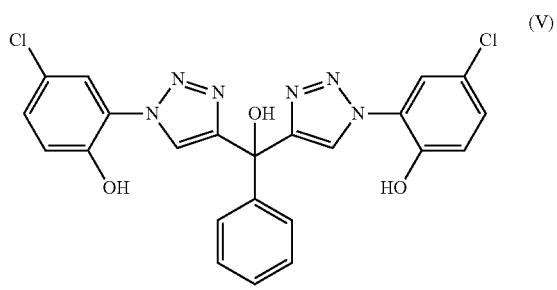

(V)

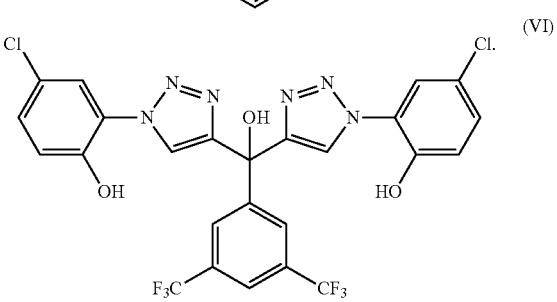

(VI)

8. A pharmaceutical composition, comprising the compound of claim 1, or a pharmaceutically acceptable salt thereof, and a pharmaceutically acceptable carrier.
9. A pharmaceutical composition, comprising the compound of claim 6, or a pharmaceutically acceptable salt thereof, and a pharmaceutically acceptable carrier.
10. A pharmaceutical composition, comprising the compound of claim 7, or a pharmaceutically acceptable salt thereof, and a pharmaceutically acceptable carrier.
11. A method of treating a cancer, comprising administering to a subject in need thereof a therapeutically effective amount of the compound of claim 1, or a pharmaceutically acceptable salt thereof, wherein X is O; each of $R^1$ and $R^2$ is methyl, or each of $R^1$ and $R_2$ is —$CF_3$; and the subject has a cancer selected from the group consisting of ovarian cancer, glioblastoma, breast cancer, and prostate cancer.
12. A method of treating a cancer, comprising administering to a subject in need thereof a therapeutically effective amount of the compound of claim 6, or a pharmaceutically acceptable salt thereof, wherein the subject has a cancer selected from the group consisting of ovarian cancer, glioblastoma, breast cancer, and prostate cancer.
13. A method of treating a cancer, comprising administering to a subject in need thereof a therapeutically effective amount of the compound of claim 7, or a pharmaceutically acceptable salt thereof, wherein the subject has a cancer selected from the group consisting of ovarian cancer, glioblastoma, breast cancer, and prostate cancer.
14. A method of treating a cancer, comprising administering to a subject in need thereof a therapeutically effective amount of the compound represented by formula (IV), or a pharmaceutically acceptable salt thereof

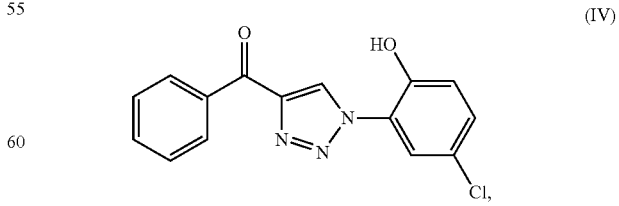

(IV)

wherein the subject has a cancer selected from the group consisting of ovarian cancer, glioblastoma, breast cancer, and prostate cancer.

* * * * *